United States Patent
Hsiung et al.

(10) Patent No.: US 12,220,214 B2
(45) Date of Patent: *Feb. 11, 2025

(54) BASELINE CORRECTION AND EXTRACTION OF HEARTBEAT PROFILES

(71) Applicant: VIAVI Solutions Inc., Chandler, AZ (US)

(72) Inventors: Chang Meng Hsiung, Redwood City, CA (US); Lan Sun, Santa Rosa, CA (US); Marc K. Von Gunten, Novato, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,273

(22) Filed: Nov. 13, 2023

(65) Prior Publication Data

US 2024/0074669 A1    Mar. 7, 2024

Related U.S. Application Data

(63) Continuation of application No. 17/823,083, filed on Aug. 30, 2022, now Pat. No. 11,918,328, which is a
(Continued)

(51) Int. Cl.
| | |
|---|---|
| A61B 5/02 | (2006.01) |
| A61B 5/024 | (2006.01) |
| A61B 5/00 | (2006.01) |

(52) U.S. Cl.
CPC .......... *A61B 5/02416* (2013.01); *A61B 5/681* (2013.01)

(58) Field of Classification Search
CPC .................................................. A61B 5/024
See application file for complete search history.

(56) References Cited

U.S. PATENT DOCUMENTS

| | | |
|---|---|---|
| 10,542,894 B2 | 1/2020 | Zhao et al. |
| 10,687,718 B2 | 6/2020 | Allec et al. |

(Continued)

FOREIGN PATENT DOCUMENTS

| | | |
|---|---|---|
| CN | 108778105 A | 11/2018 |
| CN | 109152530 A | 1/2019 |

(Continued)

OTHER PUBLICATIONS

International Search Report and Written Opinion for Application No. PCT/US2020/017063, mailed on Apr. 29, 2020, 16 pages.

(Continued)

*Primary Examiner* — Travis R Hunnings
(74) *Attorney, Agent, or Firm* — Harrity & Harrity, LLP

(57) ABSTRACT

A device may determine end-of-phase information for a plurality of wavelength channels of photoplethysmography (PPG) data. The device may calculate a set of baseline correction points for each wavelength channel of the plurality of wavelength channels. The set of baseline correction points may be calculated based on end-of-phase information for a wavelength channel of the plurality of wavelength channels and PPG data associated with the wavelength channel. The device may perform a baseline correction for each wavelength channel of the plurality of wavelength channels. A baseline correction may be performed for the wavelength channel based on the set of baseline correction points associated with the wavelength channel and the PPG data associated with the wavelength channel. The device may generate a baseline corrected heartbeat profile using a principal component analysis of a result of baseline correcting each wavelength channel of the plurality of wavelength channels.

20 Claims, 21 Drawing Sheets

Related U.S. Application Data continuation of application No. 16/780,406, filed on Feb. 3, 2020, now Pat. No. 11,445,927.

(60) Provisional application No. 62/805,170, filed on Feb. 13, 2019.

(56) References Cited

U.S. PATENT DOCUMENTS

| | | |
|---|---|---|
| 11,445,927 B2 | 9/2022 | Hsiung et al. |
| 11,918,328 B2 * | 3/2024 | Hsiung ................ A61B 5/7278 |
| 2014/0275852 A1 | 9/2014 | Hong et al. |
| 2014/0276119 A1 | 9/2014 | Venkatraman et al. |
| 2015/0112158 A1 | 4/2015 | He et al. |
| 2015/0112208 A1 | 4/2015 | He et al. |
| 2016/0231235 A1 | 8/2016 | Gulati et al. |
| 2017/0035308 A1 | 2/2017 | Gulati et al. |
| 2019/0021615 A1 | 1/2019 | Rundo et al. |
| 2020/0253492 A1 * | 8/2020 | Hsiung ................ A61B 5/7203 |
| 2021/0093277 A1 * | 4/2021 | Jackson ................ A61B 5/7292 |
| 2022/0409076 A1 | 12/2022 | Hsiung et al. |

FOREIGN PATENT DOCUMENTS

| | | |
|---|---|---|
| EP | 1297784 A1 | 4/2003 |
| EP | 3205262 A1 | 8/2017 |
| TW | M486395 U | 9/2014 |
| WO | 2017087417 A1 | 5/2017 |

OTHER PUBLICATIONS

Zaidi S.N., et al., "Orthostatic Stress And Area Under The Curve of Photoplethysmography Waveform", Biomedical Physics And Engineering Express, Jul. 28, 2016, vol. 2(4), pp. 045006, 13 pages.

* cited by examiner

BASELINE CORRECTION AND EXTRACTION OF HEARTBEAT PROFILES

RELATED APPLICATION

This application is a continuation of U.S. patent application Ser. No. 17/823,083, filed Aug. 30, 2022, which is a continuation of U.S. patent application Ser. No. 16/780,406, filed Feb. 3, 2020, which claims priority to U.S. Provisional Patent Application No. 62/805,170, filed on Feb. 13, 2019, the contents of which are incorporated herein by reference in their entireties.

BACKGROUND

Photoplethysmography (PPG) is an optical technique that can be used to detect volumetric changes in blood in peripheral circulation (as blood volume changes due to the pumping action of the heart). PPG is a non-invasive method that makes measurements at the surface of the skin (e.g., at a fingertip, a wrist, an ear lobe, and/or the like). A PPG device may take the form of, for example, a multispectral sensor device (e.g., a binary multispectral (BMS) sensor device) that provides heartbeat time-series data associated with multiple wavelength channels (e.g., 64 wavelength channels). The multispectral sensor device may include multiple sensor elements (e.g., optical sensors, spectral sensors, and/or image sensors), each to receive one of the multiple wavelength channels (via a respective region of a multispectral filter) in order to capture the heartbeat time-series data.

SUMMARY

According to some implementations, a method may include determining, by a device, end-of-phase information for a plurality of wavelength channels of PPG data; calculating, by the device, a set of baseline correction points for each wavelength channel of the plurality of wavelength channels, wherein a set of baseline correction points is calculated based on end-of-phase information for a wavelength channel of the plurality of wavelength channels and PPG data associated with the wavelength channel; performing, by the device, a baseline correction for each wavelength channel of the plurality of wavelength channels, wherein a baseline correction is performed for the wavelength channel based on the set of baseline correction points associated with the wavelength channel and the PPG data associated with the wavelength channel; and generating, by the device, a baseline corrected heartbeat profile using a principal component analysis of a result of baseline correcting each wavelength channel of the plurality of wavelength channels.

According to some implementations, a device may include one or more memories, and one or more processors, communicatively coupled to the one or more memories, configured to: determine end-of-phase information for a plurality of wavelength channels of PPG data; calculate a set of baseline correction points for each wavelength channel of the plurality of wavelength channels, wherein a set of baseline correction points is calculated based on end-of-phase information for a wavelength channel of the plurality of wavelength channels and PPG data associated with the wavelength channel; perform a baseline correction for each wavelength channel of the plurality of wavelength channels, wherein a baseline correction is performed for the wavelength channel based on the set of baseline correction points associated with the wavelength channel and the PPG data associated with the wavelength channel; and generate a baseline corrected heartbeat profile using a principal component analysis of a result of baseline correcting each wavelength channel of the plurality of wavelength channels.

According to some implementations, a non-transitory computer-readable medium may store one or more instructions. The one or more instructions, when executed by one or more processors of a device, may cause the one or more processors to: determine end-of-phase information for a plurality of wavelength channels of PPG data; calculate a set of baseline correction points for each wavelength channel of the plurality of wavelength channels, wherein a set of baseline correction points is calculated based on end-of-phase information for a wavelength channel of the plurality of wavelength channels and PPG data associated with the wavelength channel; perform a baseline correction for each wavelength channel of the plurality of wavelength channels, wherein a baseline correction is performed for the wavelength channel based on the set of baseline correction points associated with the wavelength channel and the PPG data associated with the wavelength channel; and generate a baseline corrected heartbeat profile using a principal component analysis of a result of baseline correcting each wavelength channel of the plurality of wavelength channels.

DETAILED DESCRIPTION

Figure 1:
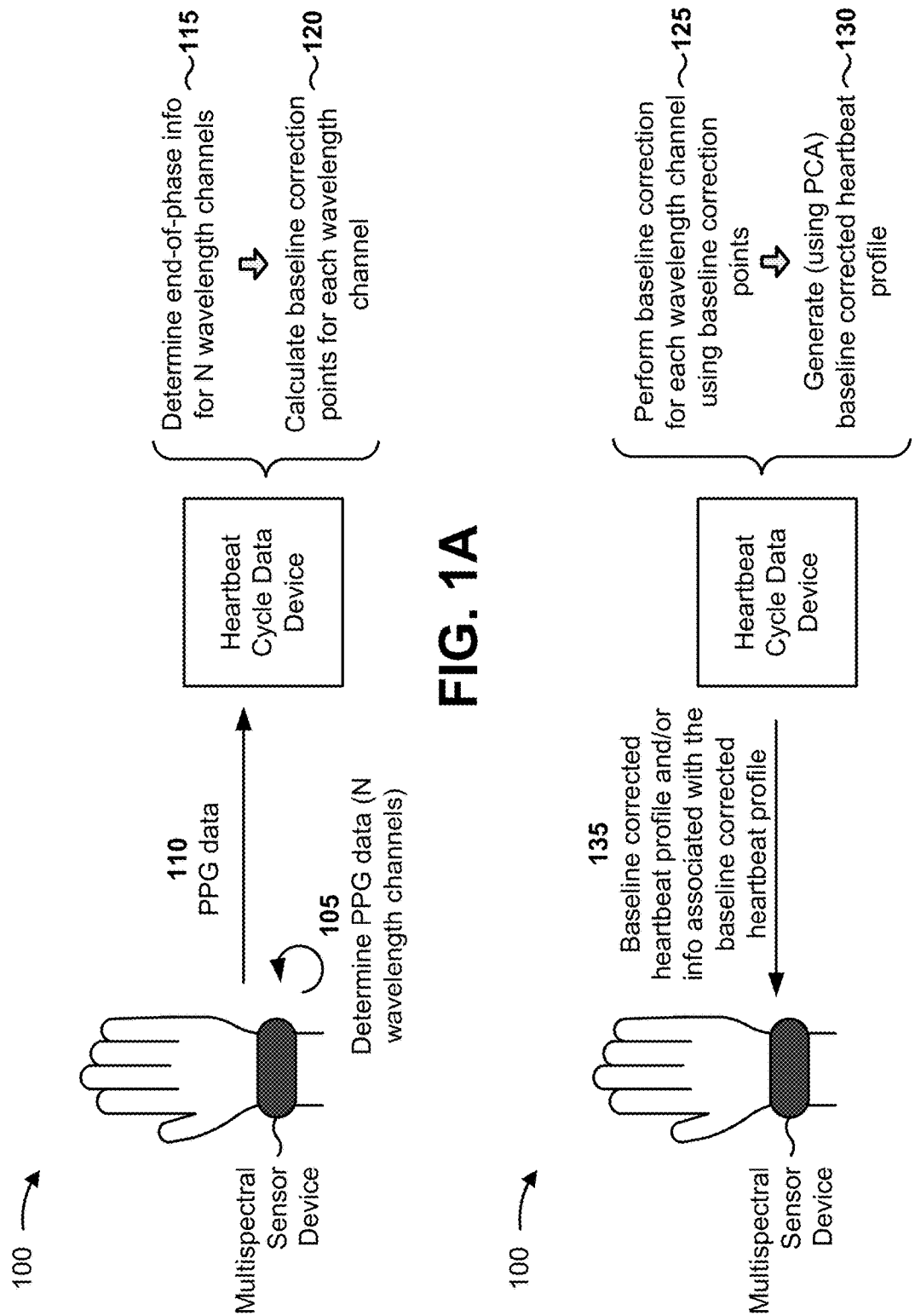
FIGS. 1A and 1B are diagrams of an example implementation described herein.

The following detailed description of example implementations refers to the accompanying drawings. The same reference numbers in different drawings may identify the same or similar elements. Further, while the following description may use a multispectral sensor device in an example, the principles, procedures, operations, techniques, and methods described herein may be used with any other type of sensing device, such as a spectrometer, an optical sensor, a spectral sensor, and/or the like.

As described above, a multispectral sensor device may be capable of measuring, obtaining, collecting, or otherwise determining heartbeat time-series data associated with multiple (e.g., 16, 32, 64, and/or the like) wavelength channels. Such data is herein referred to as PPG data. In practice the PPG data can be quite noisy, and can include a sloping baseline (e.g., ascending, descending, or both) and/or a baseline shift that obscures the signal. Due to such noise and/or baseline issues, segmenting the PPG data into systolic phases (e.g., times during which the heart is contracting) and diastolic phases (e.g., times during which the heart is resting) can be difficult. Thus, it is often difficult to use the PPG data in association with performing a biometric monitoring action because the raw PPG data may lead to inaccurate, unreliable results.

In some cases, PPG data can be processed in order to determine heartbeat cycle data that identifies start and end times of heartbeat cycles. It is then possible to perform a biometric monitoring action based on this heartbeat cycle data. However, sloping baselines and/or baseline shifts may still be present in the heartbeat cycle data, which can negatively impact accuracy and/or reliability associated with the biometric monitoring action.

Some implementations described herein provide a device capable of generating a baseline corrected heartbeat profile. The baseline corrected heartbeat profile is a heartbeat profile for which sloping baselines and/or baseline shifts have been at least partially corrected (e.g., so as to reduce or eliminate an impact of the sloping baselines and/or baseline shifts on the heartbeat profile). In some implementations, the baseline corrected heartbeat profile can be generated based on a plurality of wavelength channels of PPG data (e.g., 64 channels of PPG data). In some implementations, a baseline correction may be performed for each of the plurality of wavelength channels, after which a baseline corrected heartbeat profile can be generated using a principal component analysis. Additional details regarding generation of the baseline corrected heartbeat profile are described below.

In some implementations, the baseline corrected heartbeat profile can be used in association with performing a biometric monitoring action, such as vital sign monitoring (e.g., instantaneous heart rate determination, blood pressure determination, and/or the like), or another type of biometric determination and/or monitoring (e.g., blood oxygenation determination, augmentation index determination, hydration determination, and/or the like). Here, performing the biometric monitoring action using the baseline corrected heartbeat profile may improve accuracy and/or reliability of a result of the biometric monitoring action (e.g., as compared to using raw PPG data or as compared to using heartbeat cycle data that has not been baseline corrected).

FIGS. 1A and 1B are diagrams of an example implementation 100 described herein.

As shown in FIG. 1A, a multispectral sensor device may be positioned relative to a skin surface of a subject. For example, as shown in FIG. 1A, the multispectral sensor device may be a device worn on the wrist of the subject. In some implementations, the multispectral sensor device may be positioned relative to the skin surface at another location on the body, such as on a fingertip, an arm, a leg, an ear lobe, and/or the like. In some implementations, the multispectral sensor device includes a BMS sensing device that operates in, for example, the visible (VIS) spectrum, the near infrared (NIR) spectrum, and/or the like.

As shown by reference 105, the multispectral sensor device may determine (e.g., measure, gather, collect, and/or the like) PPG data (e.g., raw heartbeat data) associated with N (N>1) wavelength channels. The PPG data includes, for each of the N wavelength channels, photometric response data that indicates a blood volume beneath the skin surface at the location of the multispectral sensor device at a given time point.

As shown by reference number 110, a heartbeat cycle data device may obtain the PPG data from the multispectral sensor device. The heartbeat cycle data device is a device capable of generating a baseline corrected heartbeat profile, as described herein. In some implementations, the heartbeat cycle data device may be integrated with the multispectral sensor device (e.g., in a same package, a same housing, on a same chip, and/or the like). Alternatively, the heartbeat cycle data device may be separate (e.g., remotely located) from the multispectral sensor device.

In some implementations, the heartbeat cycle data device may obtain the PPG data in real-time or near real-time (e.g., when the multispectral sensor device is configured to provide the PPG data as the multispectral sensor device obtains the PPG data). Additionally, or alternatively, the heartbeat cycle data device may obtain the PPG data based on the multispectral sensor device (e.g., automatically) providing the PPG data on a periodic basis (e.g., every one second, every five seconds, and/or the like). Additionally, or alternatively, the heartbeat cycle data device may obtain the PPG data from the multispectral sensor device based on requesting the PPG data from the multispectral sensor device.

As shown by reference number 115, the heartbeat cycle data device may determine end-of-phase information for the N wavelength channels of the PPG data. In some implementations, the end-of-phase information may include, for each of the N wavelength channels, information that identifies end points of positive phases in the PPG data (herein referred to as ends-of-positive phases (EoPPs) and/or information that identifies end points of negative phases in the PPG data (herein referred to as ends-of-negative phases (EoNPs)). A positive phase (indicating the systolic phase of a heartbeat) in the PPG data and an adjacent negative phase (indicating the diastolic phase of the heartbeat) defines one heartbeat cycle period. Therefore, start and end times of heartbeat cycles can be defined by EoNPs and EoPPs in the PPG data.

In some implementations, the heartbeat cycle data device may determine the end-of-phase information by determining heartbeat cycle data based on the PPG data. For example, in some implementations, the heartbeat cycle data device may determine heartbeat cycle data that identifies start and end points of heartbeat cycles indicated by the PPG data and, therefore, may determine EoNPs and EoPPs for each wavelength channel in the PPG data. In some implementations, the heartbeat cycle data device may use feature vectors based on moving slopes to determine the EoPPs and EoNPs in the PPG data for each wavelength channel. In some implementations, the heartbeat cycle data device may determine the heartbeat cycle data in a manner described in U.S. patent application Ser. No. 16/210,740, filed on Dec. 8, 2018, and entitled "AUTONOMOUS FULL SPECTRUM BIOMETRIC MONITORING," the content of which is incorporated by reference herein in its entirety.

As shown by reference 120, the heartbeat cycle data device may calculate a set of baseline correction points for each of the N wavelength channels. A set of baseline correction points, associated with a given wavelength channel, includes a set of points that define a baseline of the PPG data for the given wavelength channel. In some implementations, the heartbeat cycle data device may calculate the set of baseline correction points for a given wavelength channel based on end-of-phase information (e.g., EoNPs and/or EoPPs) for the given wavelength channel and PPG data associated with the given wavelength channel.

In some implementations, for a given wavelength channel, the set of baseline correction points may be a set of trough points (e.g., true trough points) of the given wavelength channel. In such a case, the heartbeat cycle data device may calculate the set of baseline correction points based on end-of-phase information that identifies EoNPs associated with the given wavelength channel. In some implementations, the heartbeat cycle data device may derive the set of trough points for a given wavelength channel based on searching for minima points between EoNP timesteps versus wFV time steps prior to the EoNP time steps. Here, wFV is a window width of a feature vector based on which the heartbeat cycle data is determined. That is, in some implementations, the set of trough points for a given wavelength channel may be determined based on moving slopes transformed data, where wFV is a setting associated with the transformation. In some implementations, the heartbeat cycle data device may perform baseline correction using only the set of trough points, as described below.

Alternatively, in some implementations, for a given wavelength channel, the set of baseline correction points may be a set of peak points (e.g., true peak points) of the given wavelength channel. In such a case, the heartbeat cycle data device may calculate the set of baseline correction points based on end-of-phase information that identifies EoPPs associated with the given wavelength channel. In some implementations, the heartbeat cycle data device may derive the set of peak points for a given wavelength channel based on searching for maxima points between EoPP timesteps versus wFV time steps prior to the EoPP time steps. In some implementations, the heartbeat cycle data device may perform baseline correction using only the set of peak points, as described below. That is, in some implementations, the set of peak points for a given wavelength channel may be determined based on moving slopes transformed data, where wFV is a setting associated with the transformation.

Alternatively, in some implementations, for a given wavelength channel, the set of baseline correction points may be a set of centerline points for the given wavelength channel. In such a case, the heartbeat cycle data device may calculate the set of baseline correction points based on end-of-phase information that identifies EoPPs associated with the given wavelength channel and information that identifies EoNPs associated with the given wavelength channel. In some implementations, the heartbeat cycle data device may determine the set of centerline points for the given wavelength channel based on a set of trough points (e.g., derived based on the EoNPs associated with the given wavelength channel) and a set of peak points (e.g., derived based on the EoPPs associated with the given wavelength channel). An example of calculating a set of centerline points is provided below with regard to FIG. 2. In some implementations, the heartbeat cycle data device may perform baseline correction using only the centerline points, as described below.

As shown by reference 125, the heartbeat cycle data device may perform a baseline correction for each of the N wavelength channels. In some implementations, the heartbeat cycle data device may perform a baseline correction for a given wavelength channel based on the set of baseline correction points (e.g., the set of trough points, the set of peak points, or the set of centerline points) associated with the given wavelength channel and the PPG data associated with the given wavelength channel. In some implementations, the heartbeat cycle data device may perform the baseline correction based on subtracting a baseline, defined by the set of baseline correction points, from the PPG data curve. For example, for a given wavelength channel, the heartbeat cycle data device may form a baseline by connecting the set of baseline correction points (e.g., the set of trough points, the set of peak points, or the set of centerline points). Next, the heartbeat cycle data device may subtract the baseline from the PPG data curve, thereby baseline correcting the PPG data. In some implementations, the heartbeat cycle data device may perform such a baseline correction for each of the N wavelength channels.

As shown by reference 130, the heartbeat cycle data device may generate a baseline corrected heartbeat profile based on a result of baseline correcting each of the N wavelength channels. In some implementations, the heartbeat cycle data device may generate the baseline corrected heartbeat profile based on performing a principal component analysis (PCA) of the N baseline corrected wavelength channels. For example, results of baseline correcting the N wavelength channels can be provided as input to a PCA algorithm, and the PCA algorithm may provide, as an output, a first principal component (PC1) result. Here, the PC1 result may be univariate time series data (i.e., single channel data) that defines a baseline corrected heartbeat profile. The PCA acts to compress the multi-channel PPG data into univariate time series data (in the form of PC1). Notably, PC1 has a higher signal-to-noise ratio (SNR) than SNRs of individual wavelength channels and, therefore, may enable improved biometric monitoring, as illustrated below by FIGS. 6A and 6B.

In some implementations, the heartbeat cycle data device may perform a baseline correction of the baseline corrected heartbeat profile. For example, a baseline shift may result from compression to PC1 by the PCA when the heartbeat cycle data device performs baseline correction using sets of trough points for each of the N wavelength channels or when the heartbeat cycle data device performs baseline correction using sets of peak points for each of the N wavelength channels. Thus, further improvement may be provided by performing a baseline correction of the baseline corrected heartbeat profile. Here, the heartbeat cycle data device may calculate a set of baseline correction points for the baseline corrected heartbeat profile, and may perform, using the set of baseline correction points for the baseline corrected heartbeat profile, a baseline correction for the baseline corrected heartbeat profile. The determination of a set of correction points for the baseline corrected heartbeat profile and the subsequent baseline correction of the baseline corrected heartbeat profile may be performed in a similar manner as described above.

In some implementations, performing the baseline correction on the baseline corrected heartbeat profile may provide additional accuracy and/or reliability of a biometric monitoring action by reducing or eliminating the baseline shift resulting from the compression to PC1 provided by the PCA. In some implementations, one or more additional baseline corrections may be performed in order to further improve accuracy and/or reliability of a subsequently performed biometric monitoring action. Notably, when the heartbeat cycle data performs baseline correction using sets of centerline points for each of the N wavelength channels, there may be no need to perform the baseline correction of the baseline corrected heartbeat profile data (e.g., due to a characteristic of PCA that applies mean centering, which is equivalent to centerline baseline correction).

In some implementations, as shown by reference number 135, the heartbeat cycle data device may provide the baseline corrected heartbeat profile and/or information associated with the baseline corrected heartbeat profile. For example, in some implementations, the heartbeat cycle data device may provide the baseline corrected heartbeat profile to a device configured to perform vital sign monitoring (e.g., instantaneous heart rate determination, blood pressure determination, and/or the like). As another example, in some implementations, the heartbeat cycle data device may provide the baseline corrected heartbeat profile to a device configured to perform another type of biometric monitoring (e.g., blood oxygen saturation determination, hydration determination, and/or the like). In some implementations, the heartbeat cycle data device may determine an instantaneous heart rate based on the baseline corrected heartbeat profile, and may provide (e.g., for display via a display screen of the multispectral sensor device and/or the heartbeat cycle data device) information that identifies the instantaneous heart rate.

In this way, a heartbeat cycle data device can generate a baseline corrected heartbeat profile that permits a biometric monitoring action to be performed with increased accuracy and/or increased reliability (e.g., as compared to performing the biometric monitoring action based on raw PPG data, or as compared to performing the biometric monitoring action based on heartbeat cycle data that has not been baseline corrected).

As indicated above, FIGS. 1A and 1B are provided merely as examples. Other examples may differ from what is described with regard to FIGS. 1A and 1B.

Figure 2:
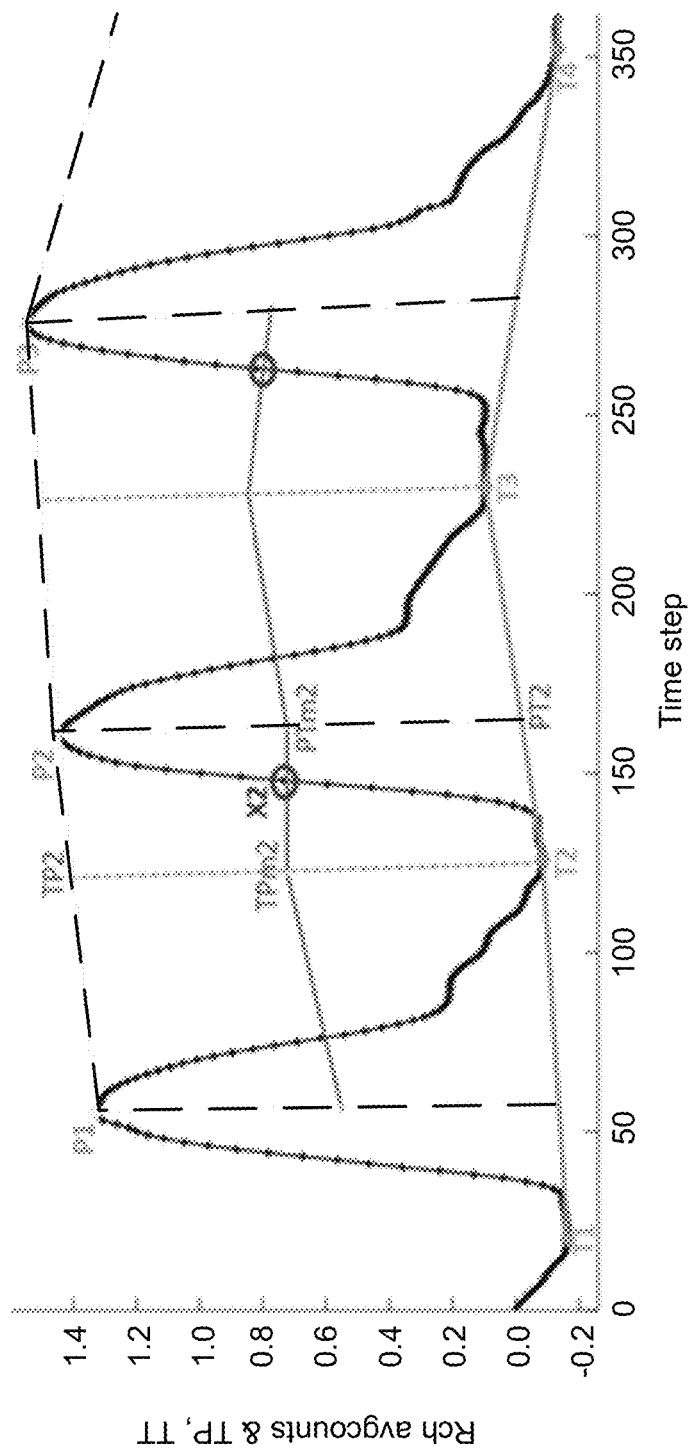
FIG. 2 is a diagram of an example of calculating a set of centerline correction points for a wavelength channel of PPG data.

FIG. 2 is a diagram of an example of calculating a set of centerline correction points for a wavelength channel of PPG data. In some implementations, as indicated in FIG. 2, a set of centerline points may be a set of points that define a baseline that is approximately midway between a baseline defined by a set of trough points for the wavelength channel and a baseline defined by a set of peak points for the wavelength channel.

In some implementations, the heartbeat cycle data may determine the set of centerline points as follows. The heartbeat cycle data device may determine a set of trough points for the wavelength channel (e.g., in the manner described above), and determine a trough baseline based on the set of trough points. In FIG. 2, the set of trough points are identified as points T1 through T4, and the solid lines connecting points T1 through T4 form the trough baseline. The heartbeat cycle data may also determine a set of peak points for the wavelength channel (e.g., in the manner described above), and determine a peak baseline based on the set of peak points. In FIG. 2, the set of peak points are identified as points P1 through P3, and the dashed lines connecting points P1 through P3 form the peak baseline.

Next, the heartbeat cycle data device may derive peak intersection points, which can be identified as a set of points at which the peak baseline is intersected by lines (e.g., vertical lines) emanating from the trough points. An example of such a peak intersection point is labeled as point TP2 in FIG. 2. Similarly, the heartbeat cycle data device may derive trough intersection points, which can be identified as a set of points at which the trough baseline is intersected by lines (e.g., vertical lines) emanating from the peak points. An example of such a trough intersection point is labeled as point PT2 in FIG. 2.

Next, the heartbeat cycle data device may determine mid-points on the lines between the peak intersection points and the associated trough points. An example of a mid-point on the line between peak intersection point TP2 and trough point T2 is labeled as TPm2 in FIG. 2. Similarly, the heartbeat cycle data device may determine mid-points on the lines between the trough intersection points and the associated peak points. An example of a mid-point on the line between trough intersection point PT2 and peak point P2 is labeled as PTm2 in FIG. 2. While not labeled in FIG. 2, other mid-points can be determined in a similar manner.

Next, the heartbeat cycle data device may form a centerline baseline by connecting the mid-points on the lines between the peak intersection points and the associated trough points, and the mid-points on the lines between the trough intersection points and the associated peak points. For example, as indicated in FIG. 2, the heartbeat cycle data device may connect point TPm2 to point PTm2, as well as other determined mid-points (not labeled in FIG. 2), to form the indicated centerline baseline.

Next, the heartbeat cycle data device may identify intersection points of the centerline baseline with the PPG data curve. An example of such an intersection is labeled as point X2 in FIG. 2. In some implementations, the intersection points of the centerline baseline with the PPG data curve may be used to identify the set of centerline correction points for the wavelength channel. For example, for a given intersection point, the heartbeat cycle data may identify a PPG data point nearest to the given intersection point, and this nearest PPG data point may be used as one of the set of centerline correction points. Thus, in some implementations, the set of centerline correction points for the given wavelength channel may include a set of PPG data points nearest to crossing points of the determined centerline. As another example, for a given intersection point, the heartbeat cycle data device may determine (e.g., using linear interpolation) an interpolated PPG data point corresponding to an exact crossing point of the centerline baseline and the PPG data curve, and this interpolated PPG data point may be used as one of the set of centerline correction points. Thus, in some implementations, the set of centerline correction points for the given wavelength channel may include a set of exact crossing points (i.e., a set of interpolated PPG data points). In some implementations, the heartbeat cycle data device may perform this process for each of the N wavelength channels.

In some implementations, the set of centerline correction points may include one or more nearest PPG data points and one or more exact crossing points. For example, the heartbeat cycle data device may use a nearest PPG data point when the distance from the intersection point to the nearest PPG data point is less than or equal to a threshold value, and may use an interpolated PPG data point when the distance from the intersection point to the nearest data point is greater than the threshold value.

As indicated above, FIG. 2 is are provided merely as an example. Other examples may differ from what is described with regard to FIG. 2.

Figure 3:
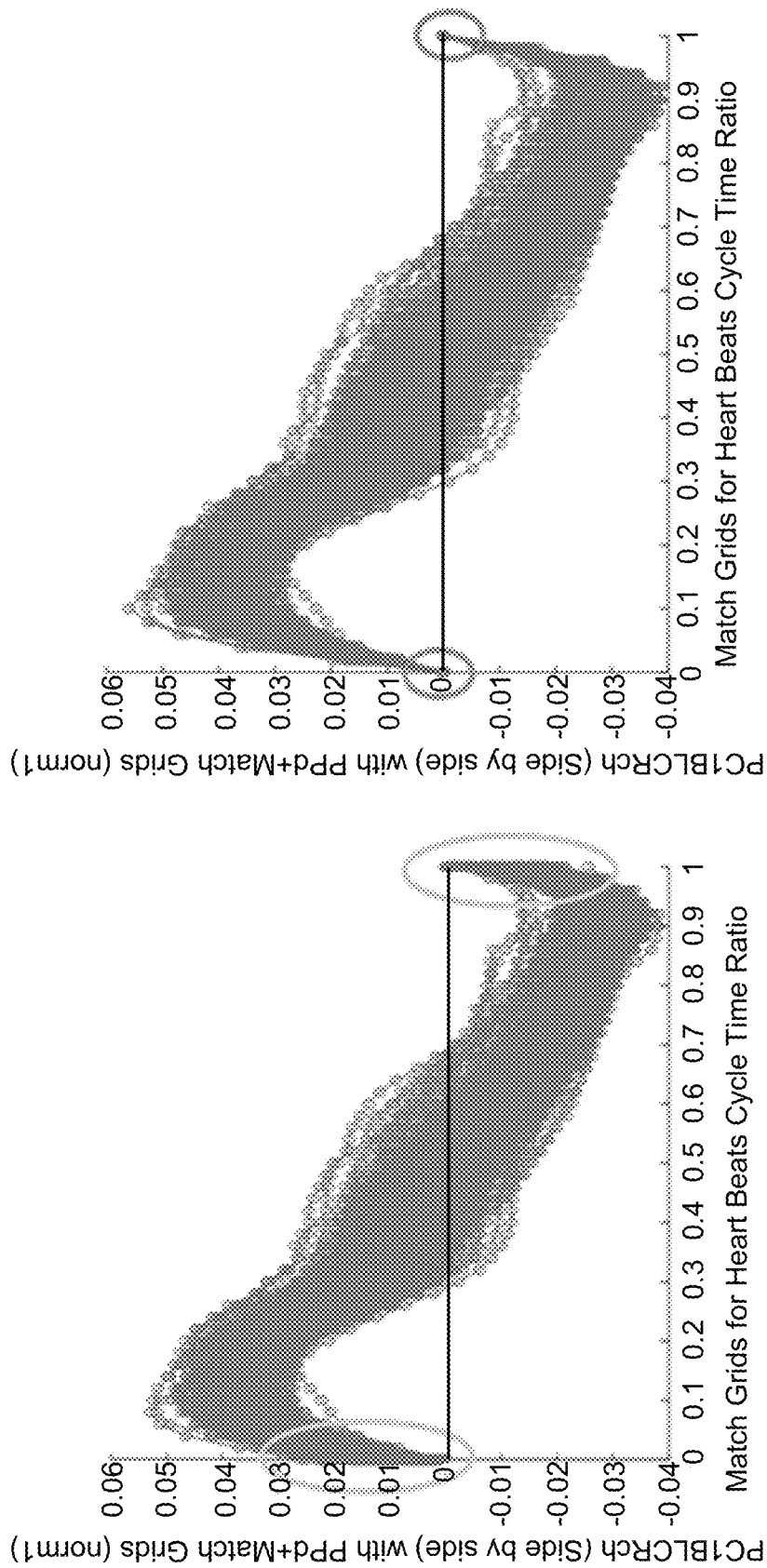
FIG. 3 is a diagram illustrating improvement provided by using centerline baseline correction with exact crossings.

In some implementations, use of one or more exact crossing points to determine the start and end points of each heartbeat cycle may provide further improvement to the baseline corrected heartbeat profile. FIG. 3 is a diagram illustrating improvement provided by using centerline baseline correction with exact crossings. In FIG. 3, lines corresponding to heartbeat cycles, associated with a centerline baseline corrected heartbeat profile, are overlaid to show starting points and ending points relative to the centerline baseline. Here, the centerline baseline is represented as a horizontal line at a value of 0. Notably, identification of individual heartbeat cycles is not necessary for understanding the concept illustrated by FIG. 3; consequently, clear delineation of each heartbeat cycle is not shown.

In the left diagram of FIG. 3, centerline baseline correction was performed without using exact crossings for determining the set of centerline points. Rather, the set of centerline points was determined using PPG data points nearest to intersections of a centerline with the PPG data curve (rather than using linear interpolation to determine exact crossing points). In the right diagram of FIG. 3, centerline baseline correction was performed using exact crossings for determining the set of centerline points. That is, the set of centerline points was determined using linear interpolation to determine exact crossing points of the centerline with the PPG data curve.

As indicated by comparing the left diagram and the right diagram in FIG. 3, the use of exact crossings for determining the set of centerline points reduces a standard deviation in a fluctuation of the start and end points of heartbeat cycles of the heartbeat profile relative to the centerline baseline. For example, start and end points of the heartbeat cycles shown in the left diagram of FIG. 3 fluctuate from the baseline in a wide range (e.g., from approximately 0.00 to approximately 0.025 for start points, and from approximately 0.00 to approximately −0.025 for end points), while start and end points of the heartbeat cycles shown in the right diagram of FIG. 3 do not fluctuate from the baseline (e.g., are equal to 0.00). Here, use of the heartbeat profile defined by the heartbeat cycles in the right diagram of FIG. 3 (i.e., the heartbeat profile that uses exact crossings for centerline baseline correction) provides improved accuracy and/or reliability for biometric monitoring due to this lack of fluctuation of start and end points of the heartbeat cycles relative to the centerline baseline.

As indicated above, FIG. 3 is provided merely as an example. Other examples may differ from what is described with regard to FIG. 3.

Figure 4A:
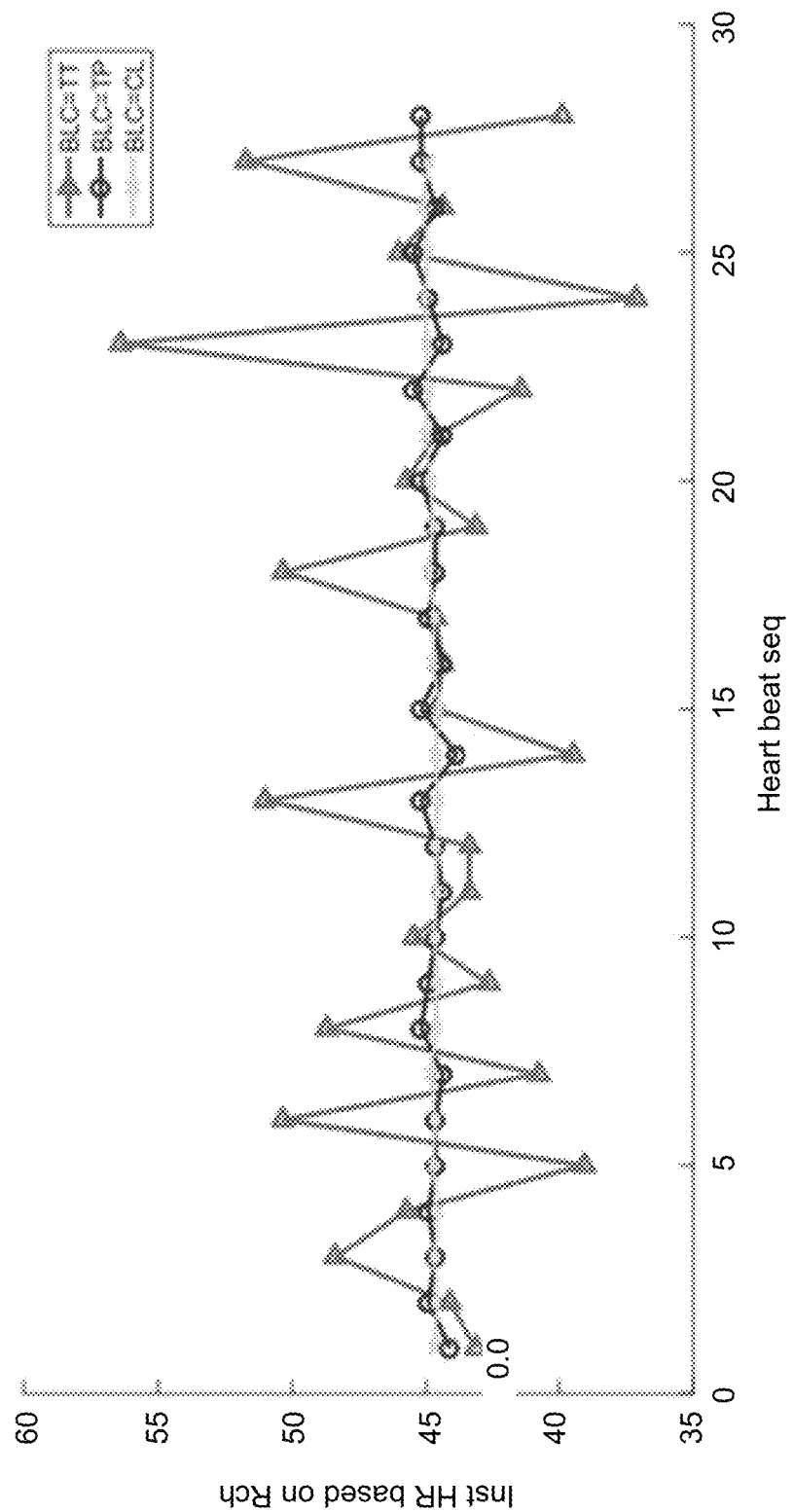
FIGS. 4A and 4B are diagrams illustrating an example of effects of the different baseline correction schemes on an estimation of heartbeat rate.
Figure 4B:
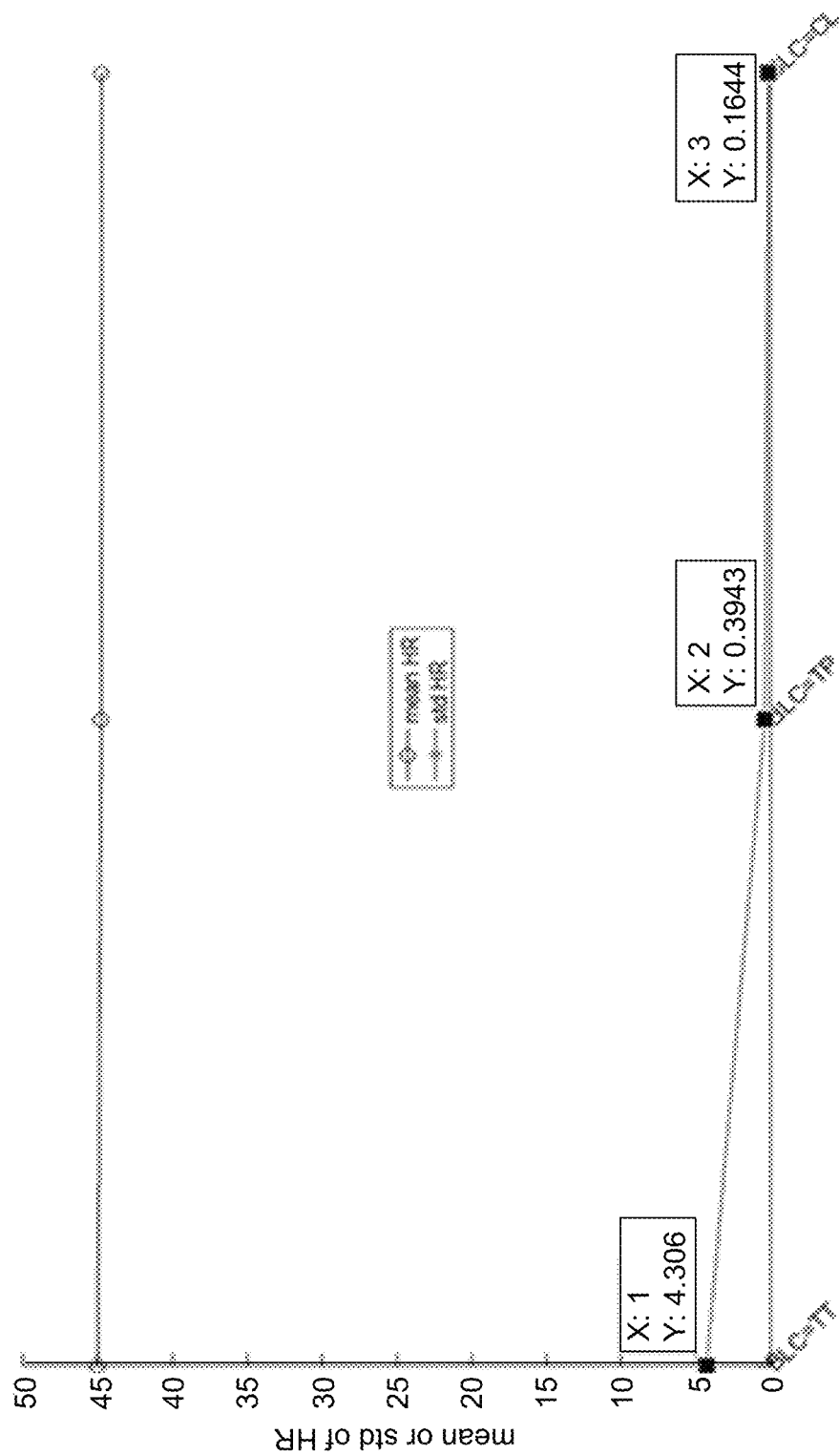

In some implementations, the baseline correction schemes described above—trough, peak, and centerline—serve the purposes of baseline correction and identifying a robust start and end time of each heartbeat cycle such that an extracted heartbeat profile will be relatively consistent and/or will not be significantly affected by environmental factors. FIGS. 4A and 4B are diagrams illustrating an example of effects of the different baseline correction schemes on an estimation of heartbeat rate. More specifically, FIG. 4A is a diagram illustrating an example of the effects of the baseline correction schemes on instantaneous heartbeat rate estimation, while FIG. 4B is a diagram illustrating an example of the effects of the baseline correction schemes on mean and standard deviation of a heartbeat rate estimation.

As illustrated in FIGS. 4A and 4B, the centerline baseline correction scheme may, in some cases, deliver a more consistent heartbeat rate estimation than the trough baseline correction scheme and the peak baseline correction scheme. This can be due to the fact that most typical heartbeat cycles show a relatively sharp anacrotic phase (i.e., ascending phase) followed by a relatively slower catacrotic phase (i.e., descending phase). In some implementations, the centerline baseline correction scheme captures these sharp inflection points during ascending phases and, hence, may deliver more precise segmentation of heartbeat cycles.

However, in some cases, use of the trough baseline correction scheme or the peak baseline correction scheme may be advantageous because implementation of the trough or peak baseline correction schemes may be faster and/or require less computing power than implementation of the centerline baseline correction scheme (while still providing an acceptable level of accuracy and/or reliability).

As indicated above, FIGS. 4A and 4B are provided merely as examples. Other examples may differ from what is described with regard to FIGS. 4A and 4B.

As described above, in some implementations, the heartbeat cycle data device may perform baseline correction for a given wavelength channel of PPG data, and may then generate a baseline corrected heartbeat profile from the baseline corrected wavelength channels using a PCA. That is, in some implementations, the heartbeat cycle data device may apply a baseline correction scheme on individual wavelength channels prior to applying a PCA to the wavelength channels (e.g., for data compression into PC1). In some implementations, baseline correcting the wavelength channels before applying the PCA to the baseline corrected wavelength channels in this manner reduces baseline shift.

Figure 5A:
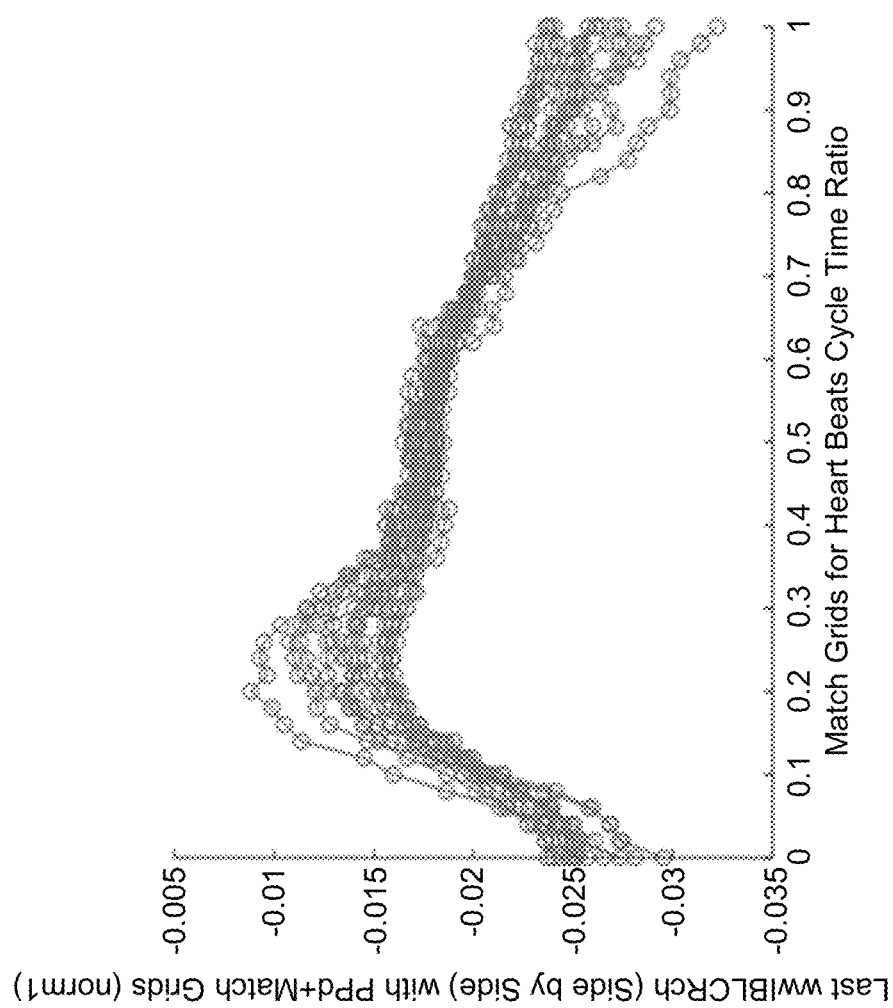
FIGS. 5A-5C are diagrams illustrating an example of improvement provided by baseline correcting the wavelength channels before applying a principal component analysis in association with generating a baseline corrected heartbeat profile.
Figure 5B:
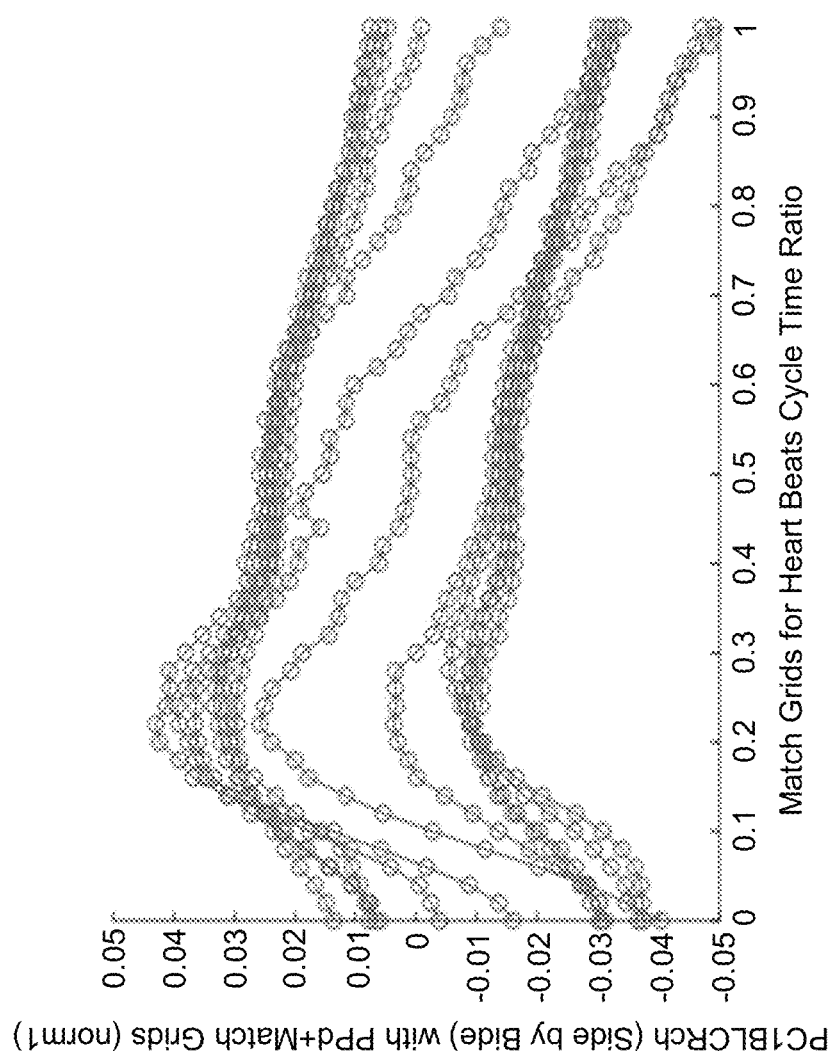
Figure 5C:
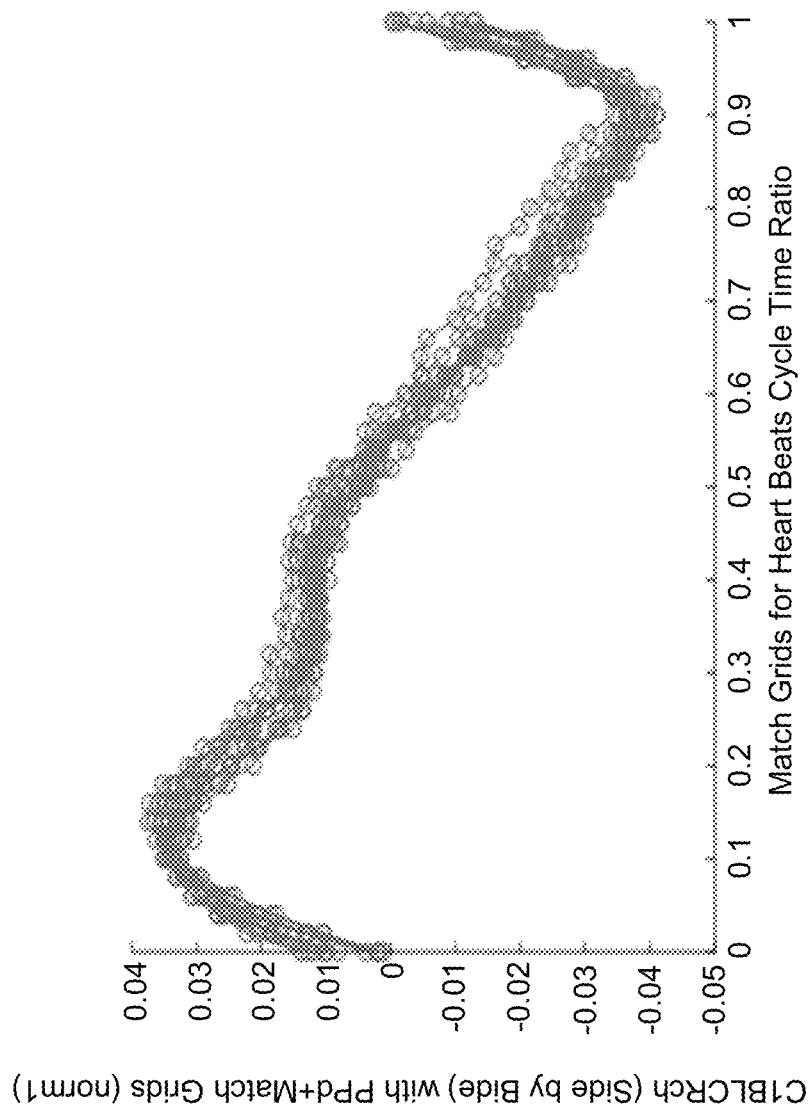

FIGS. 5A-5C are diagrams illustrating an example of improvement provided by baseline correcting the N wavelength channels before applying the PCA in association with generating the baseline corrected heartbeat profile. Notably, identification of individual signals is not necessary for understanding the implementation illustrated by FIGS. 5A-5C; consequently, clear delineation of each signal is not shown.

FIG. 5A is a diagram illustrating an example of a heartbeat profile that results when no baseline correction is performed and no PCA is performed. FIG. 5B is a diagram illustrating an example of a heartbeat profile that results when no baseline correction is performed and PCA is applied. FIG. 5C is a diagram illustrating an example of a heartbeat profile that results when baseline correction is performed, after which PCA is applied (e.g., as described in association with FIGS. 1A and 1B). In FIG. 5C, centerline baseline correction was performed on the wavelength channels. As is illustrated when comparing FIGS. 5A, 5B, and 5C, performing baseline correction and then performing PCA provides the best performance of these three options in terms of identifying relatively consistent heartbeat profiles.

As indicated above, FIGS. 5A-5C are provided merely as examples. Other examples may differ from what is described with regard to FIGS. 5A-5C.

Figure 6A:
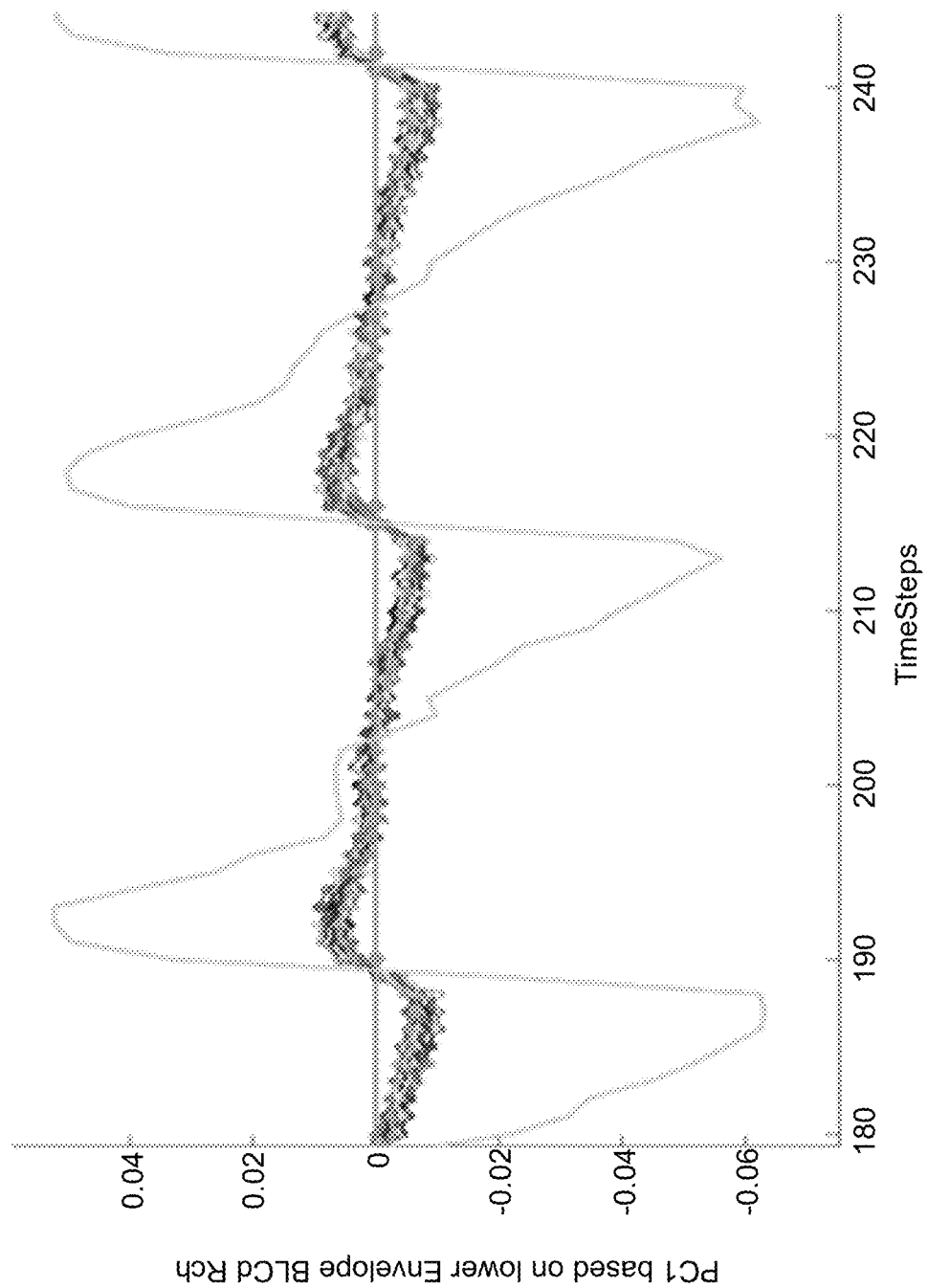
FIGS. 6A and 6B are diagrams illustrating an example of a signal-to-noise ratio improvement resulting from compression provided by performing a principal component analysis of wavelength channels in a spectrum.
Figure 6B:
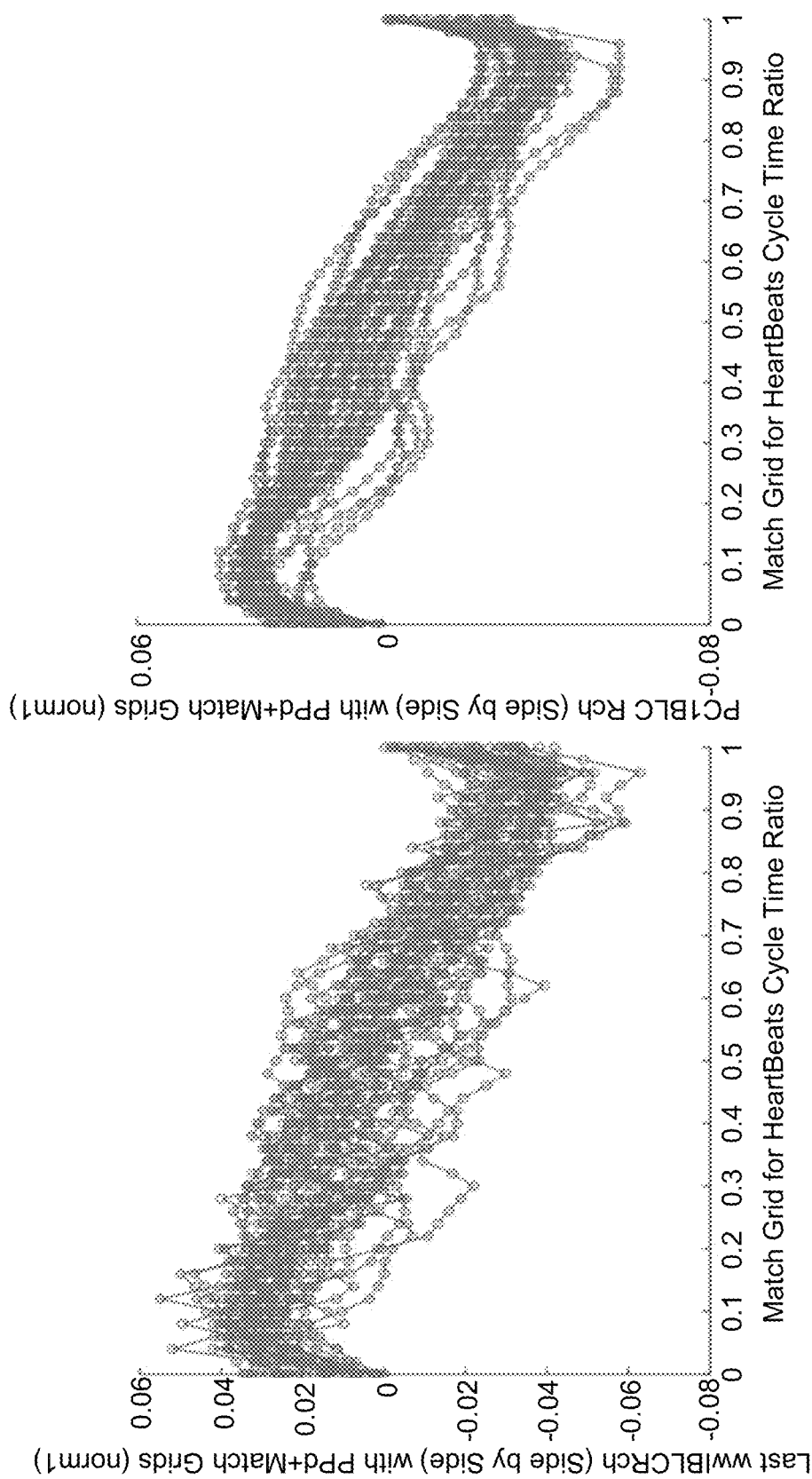

As described above, PPG data may be collected for N wavelength channels across a full spectrum (e.g., an NIR spectrum) in association with generating a baseline corrected heartbeat profile. One advantage of using PPG data across the full spectrum (rather than PPG data from a single wavelength channel in the spectrum) is improved SNR. FIGS. 6A and 6B are diagrams illustrating an example of an SNR improvement resulting from compression provided by performing a PCA on wavelength channels in a spectrum.

FIG. 6A shows two example heartbeat cycles collected by 64 individual channels (e.g., with wavelengths from 780 nanometers (nm) to 1062 nm). These lines are labeled with markers in FIG. 6A. Notably, identification of the individual wavelength channels is not necessary for understanding the implementation illustrated by FIG. 6A; consequently, clear delineation of each wavelength channel is not shown. FIG. 6A further illustrates (in a line without markers) the two example heartbeat cycles as determined based on full spectrum PPG data and using PCA compression. As can be clearly seen in FIG. 6A, the SNR in the PC1 signal is significantly higher than a SNR of any individual wavelength channel. In this example, the signal strength of PC1 may be relatively close to a theoretical value of 8 (e.g., sqrt(64)=8) times greater than that of the individual wavelength channels.

FIG. 6B shows a comparison of heartbeat cycles determined from a single channel (shown in the left portion of FIG. 6B) and heartbeat cycles determined from a PC1 based on multiple wavelength channels (shown in the right portion of FIG. 6B). Notably, identification of the individual heartbeat cycles is not necessary for understanding the implementation illustrated by FIG. 6B; consequently, clear delineation of each heartbeat cycle is not shown. As indicated by comparing the left and right portions of FIG. 6B, the heartbeat cycles determined from PC1 include comparatively less noise than those determined from the individual wavelength channel.

As indicated above, FIGS. 6A and 6B are provided merely as examples. Other examples may differ from what is described with regard to FIGS. 6A and 6B.

As described above, in some implementations, the heartbeat cycle data device may use centerline baseline correction, whereby the heartbeat cycle data device uses a set of centerline points for performing baseline correction. In some cases, when dealing with relatively noisy PPG data and applying centerline correction, there may be one or more instances when a PPG response in a descending phase does not always go down monotonically or, less commonly, one or more instances when a PPG response in an ascending phase does not go up monotonically. Such instances can result in over-divided heartbeat cycles that reduce accuracy and/or reliability of a determined heartbeat profile. Therefore, in some cases, the heartbeat cycle data device may be configured to remove these problematic instances that cause over-divided heartbeat cycles.

Figure 7A:
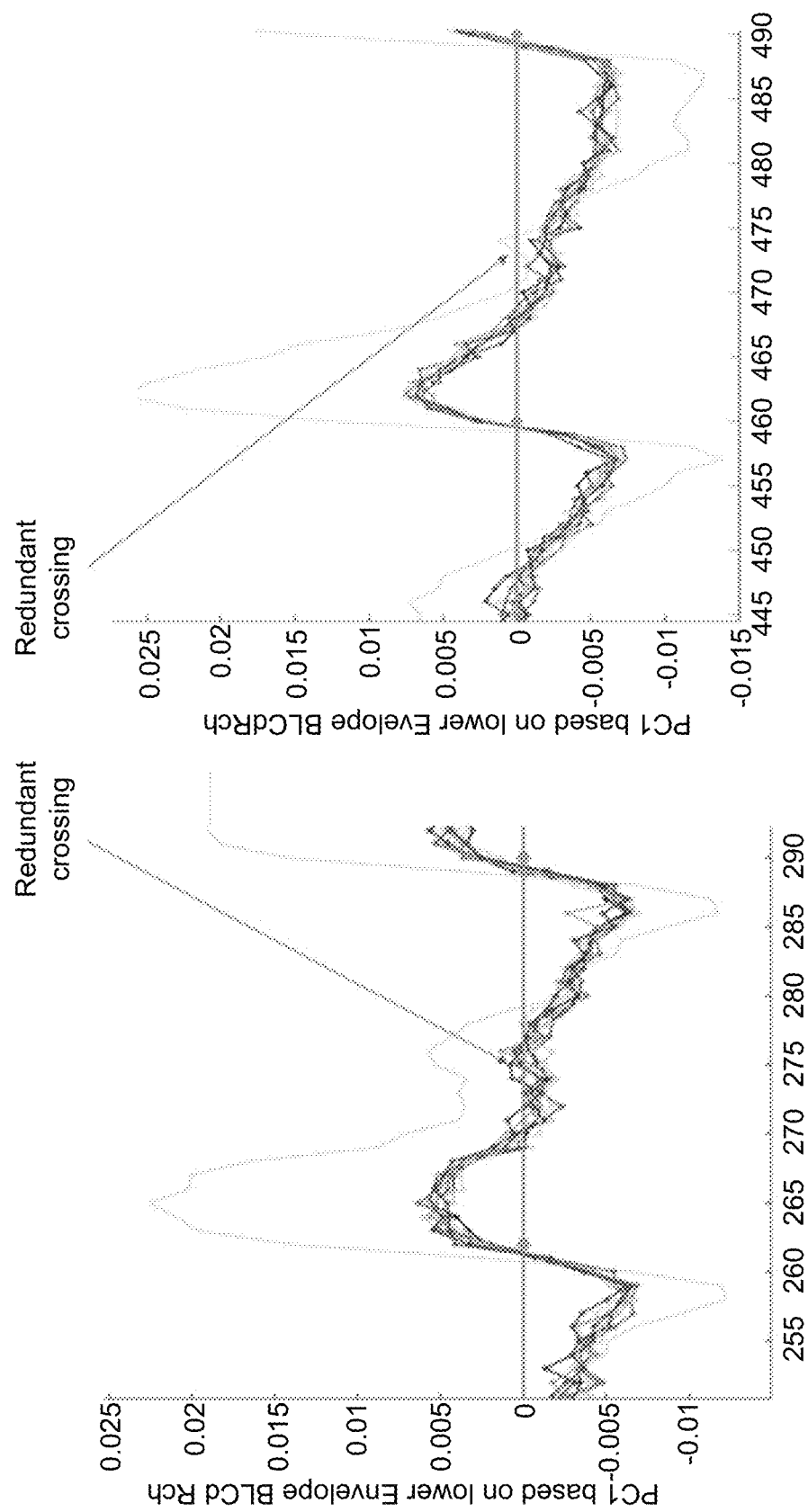
FIGS. 7A-7C are diagrams illustrating examples associated with removing redundant crossing points when applying the centerline baseline correction scheme.
Figure 7B:
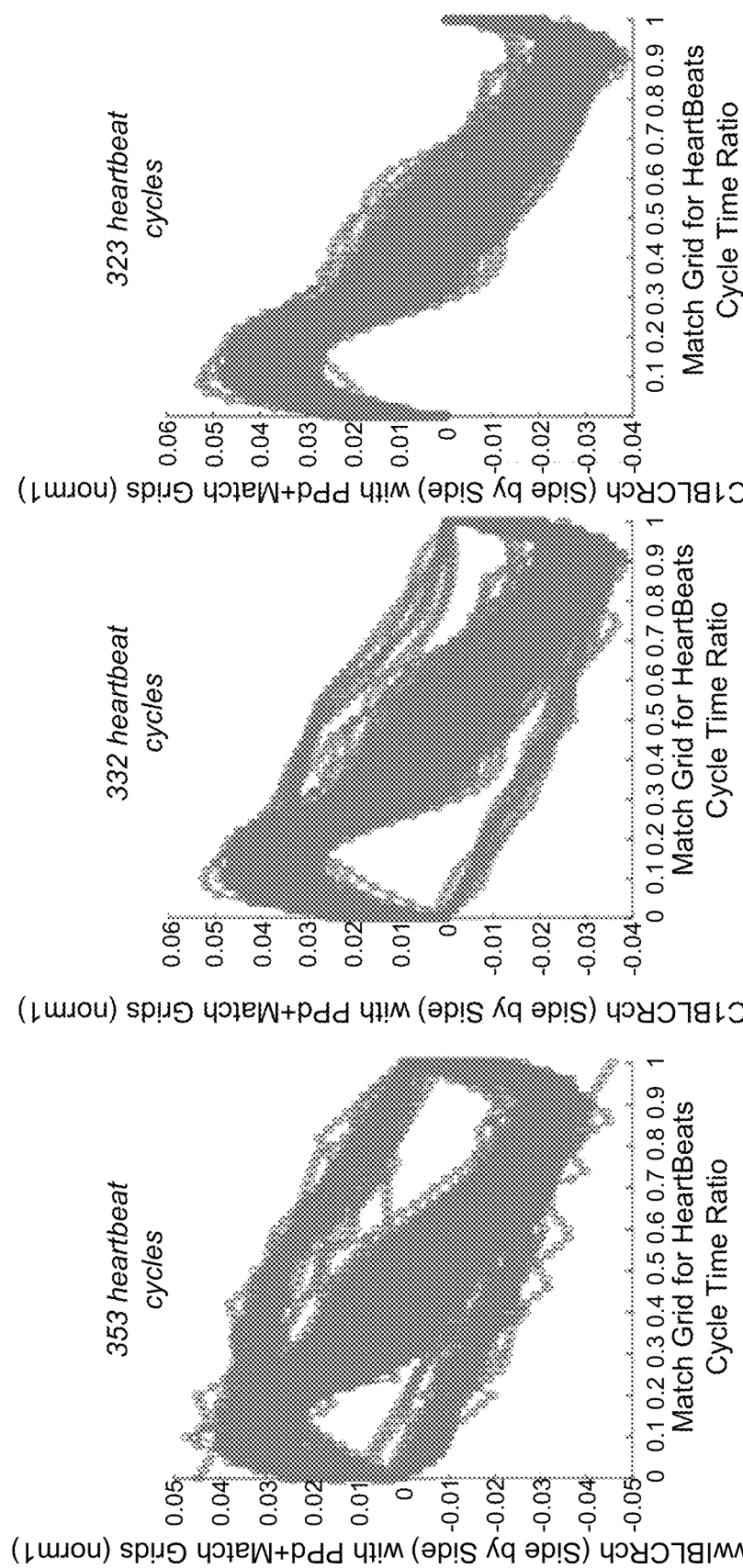
Figure 7C:
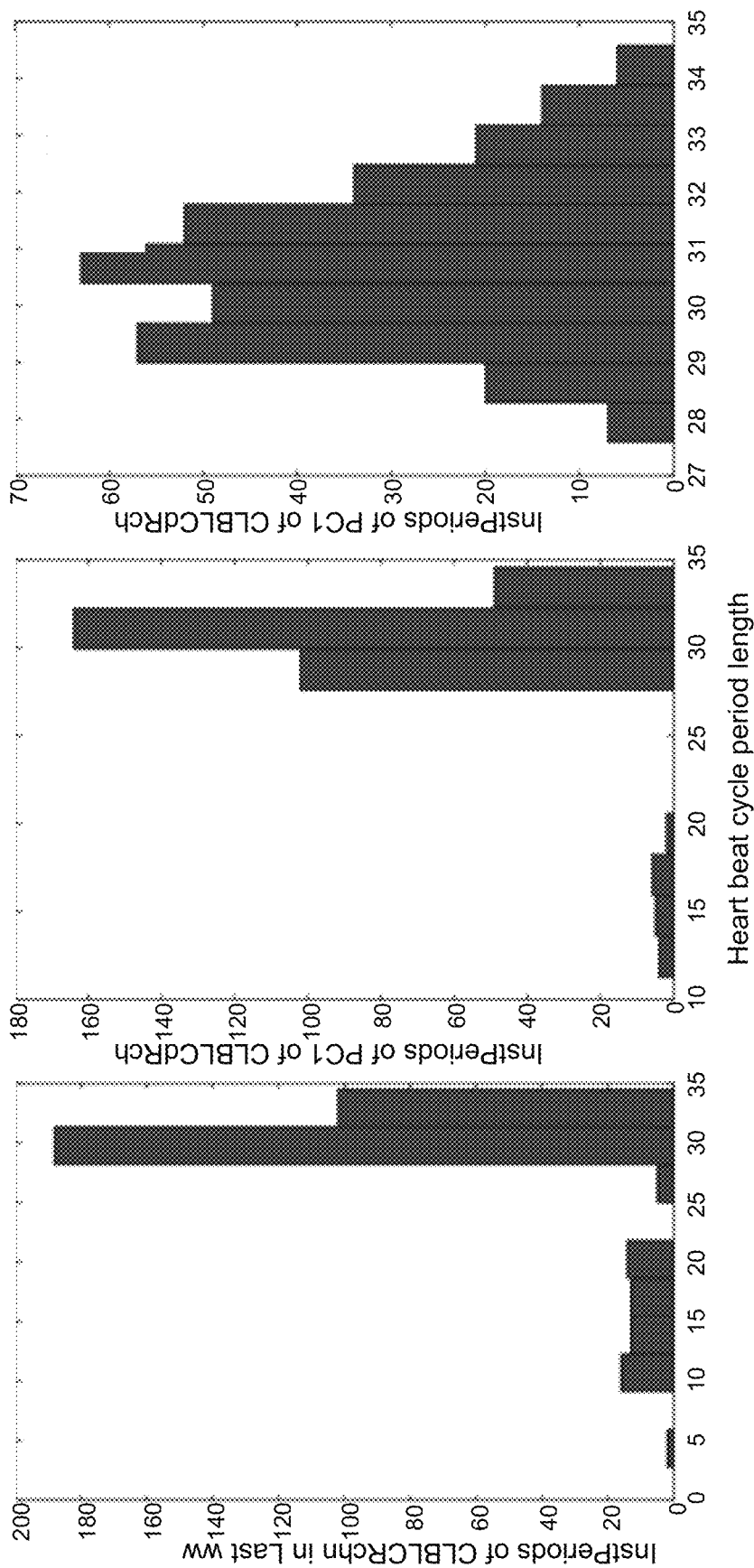

FIGS. 7A-7C are diagrams illustrating examples associated with removing redundant crossing points when applying the centerline baseline correction scheme. The left portion of FIG. 7A is a diagram depicting an example of an instance of a PPG response in an individual wavelength channel that can cause an over-divided heartbeat cycle (herein referred to as a redundant crossing), while the right portion of FIG. 7A is a diagram depicting an example of an instance of a PPG response in PC1 of multiple wavelength channels that can cause an over-divided heartbeat cycle. Notably, identification of the individual wavelength channels is not necessary for understanding the concept illustrated by FIG. 7A; consequently, clear delineation of each wavelength channel is not shown.

In some implementations, the heartbeat cycle data device may be configured to remove these problematic redundant crossings. For example, in some implementations, when determining the set of centerline points for a given wavelength channel, the heartbeat cycle data device may remove all negative-to-positive crossings between a peak point, of the set of peak points, and a subsequent trough point of the set of trough points (i.e., a descending phase), and may also remove all but a last negative-to-positive crossing between a trough point, of the set of trough points, and a subsequent peak point of the set of peak points (i.e., an ascending phase).

In some implementations, a baseline corrected heartbeat data profile generated after removal of the redundant crossings may be improved (e.g., may have a higher SNR). FIG. 7B illustrates an effect of removing the redundant crossings in the manner described above. The left and middle diagrams of FIG. 7B illustrate heartbeat cycles provided using individual wavelength channels and PC1, respectively, without implementation of the above described approach for removing redundant crossings, while the right diagram of FIG. 7B illustrates heartbeat cycles provided using PC1 results with implementation of the above described approach for removing redundant crossings. Notably, identification of the individual heartbeat cycles is not necessary for understanding the implementation illustrated by FIG. 7B; consequently, clear delineation of each heartbeat cycle is not shown.

As indicated by comparing the left and middle diagrams in FIG. 7B, PCA may provide removal of some redundant crossings that cause over-divided heartbeat cycles, even without implementation of the above described approach for removal of redundant crossings. However, implementation of the above described approach for removing redundant crossing on PC1 responses can further reduce redundant crossings that cause over-divided heartbeat cycles, as indicated by comparing the middle and right diagrams. FIG. 7C illustrates these effects in terms of a histogram of heartbeat cycle period lengths. The left, middle, and right portions of FIG. 7C correspond to the left, middle, and right portions of FIG. 7B, respectively. As can be seen in FIG. 7C, applying the above described approach for removal of redundant crossings results in a Gaussian-like distribution that is not significantly biased by redundant crossings.

As indicated above, FIGS. 7A-7C are provided merely as examples. Other examples may differ from what is described with regard to FIGS. 7A-7C.

In some implementations, when dealing with PPG data with an unstable baseline, there may be cases in which heartbeat cycles in a region of a changing baseline may be suppressed. As a result, a determined heartbeat profile in that region may have merged heartbeat cycles (and an over-sized period). In some implementations, a screening of heartbeat cycles with periods that deviate from a popular heartbeat cycle period by a threshold amount can be used to remove such outliers. FIGS. 8A-8D are diagrams illustrating examples associated with identifying and removing such heartbeat cycle outliers.

Figure 8A:
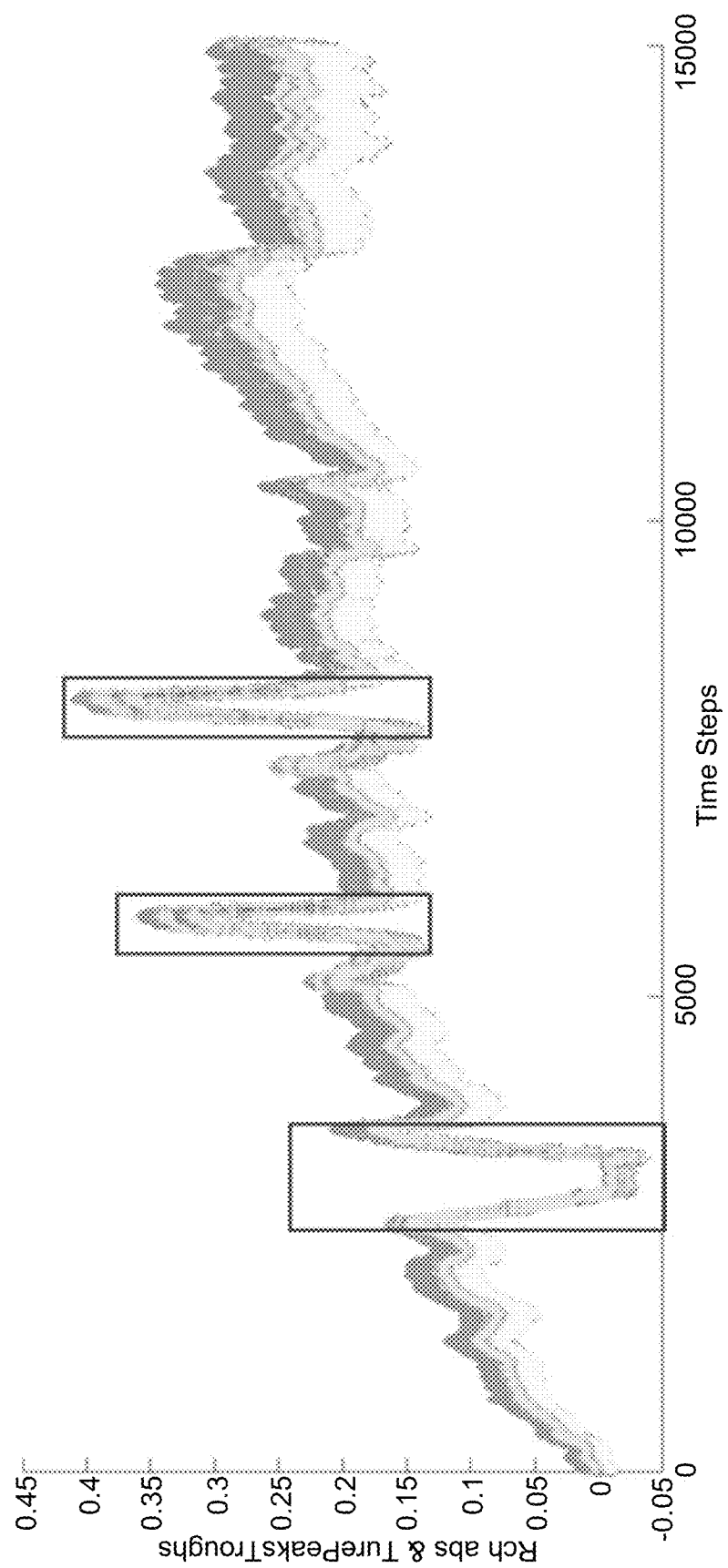
FIGS. 8A-8D are diagrams illustrating examples associated with identifying and removing heartbeat cycle outliers.
Figure 8B:
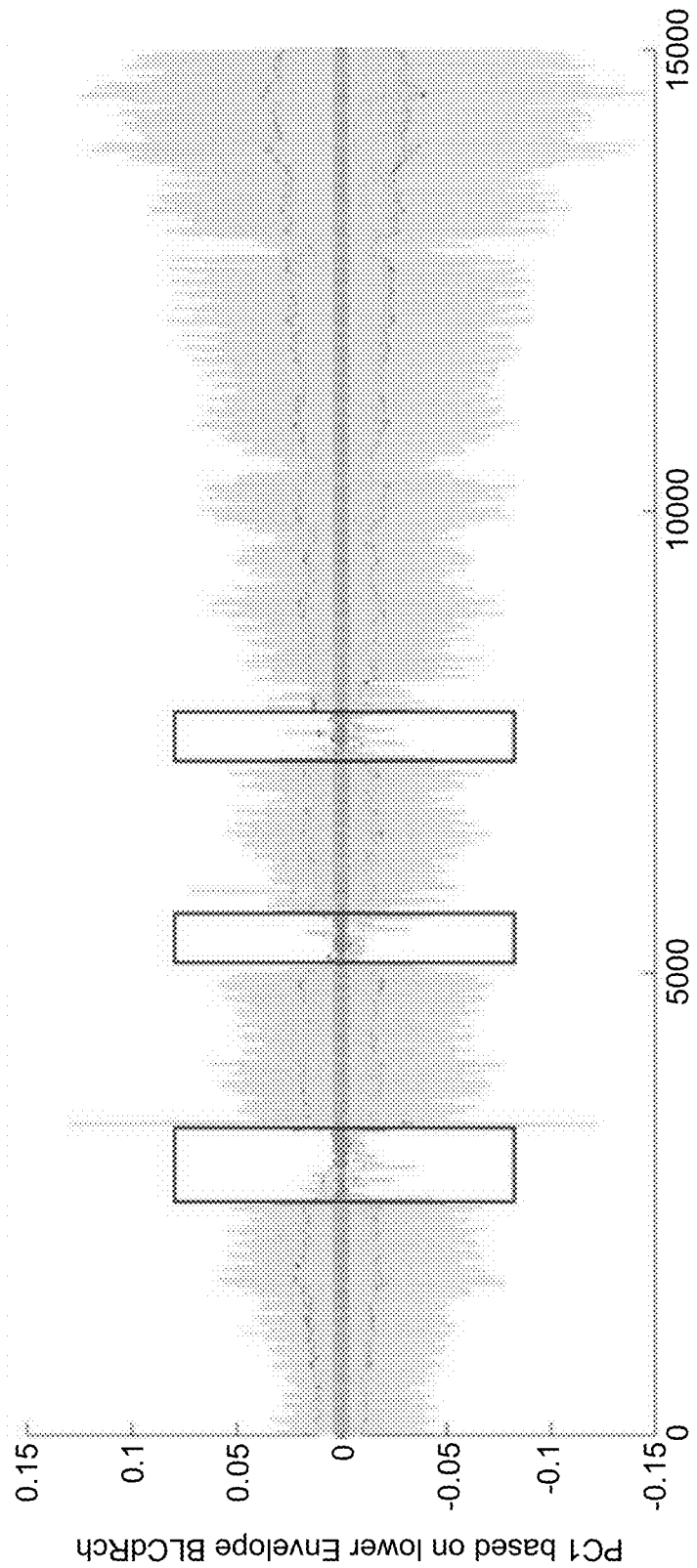

FIG. 8A illustrates an example of PPG responses of a set of wavelength channels prior to baseline correction, and FIG. 8B illustrates an example of PPG responses of the set of wavelength channels and a PC1 resulting after applying baseline correction (e.g., using centerline baseline correction). Notably, identification of the individual signals is not necessary for understanding the implementation illustrated by FIGS. 8A and 8B; consequently, clear delineation of each signal is not shown. The rectangular regions in FIGS. 8A and 8B indicate heartbeat cycles that are suppressed due to an unstable baseline, which causes the heartbeat cycles in those regions to have merged. To address such an issue, the heartbeat cycle data device may be configured to screen heartbeat cycles that have periods that differ from a particular period by a threshold amount. That is, in some implementations, the heartbeat cycle data device may identify a heartbeat cycle as a heartbeat cycle outlier, and may remove the heartbeat cycle outlier prior to generating the baseline corrected heartbeat profile. In some implementations, the heartbeat cycle data device may identify the heartbeat cycle as a heartbeat cycle outlier based on determining that a period of the heartbeat cycle differs from a popular heartbeat cycle period by an amount that satisfies a threshold. For example, the heartbeat cycle data device may be configured to identify heartbeat cycles with periods that differ from a popular heartbeat cycle period by at least two times a standard deviation of the popular heartbeat cycle period. In some implementations, the popular heartbeat cycle period may be defined as a most frequently occurring heartbeat cycle period (i.e., a mode heartbeat cycle period), an average heartbeat cycle period, a weighted average heartbeat cycle period, or using another statistical measure.

Figure 8C:
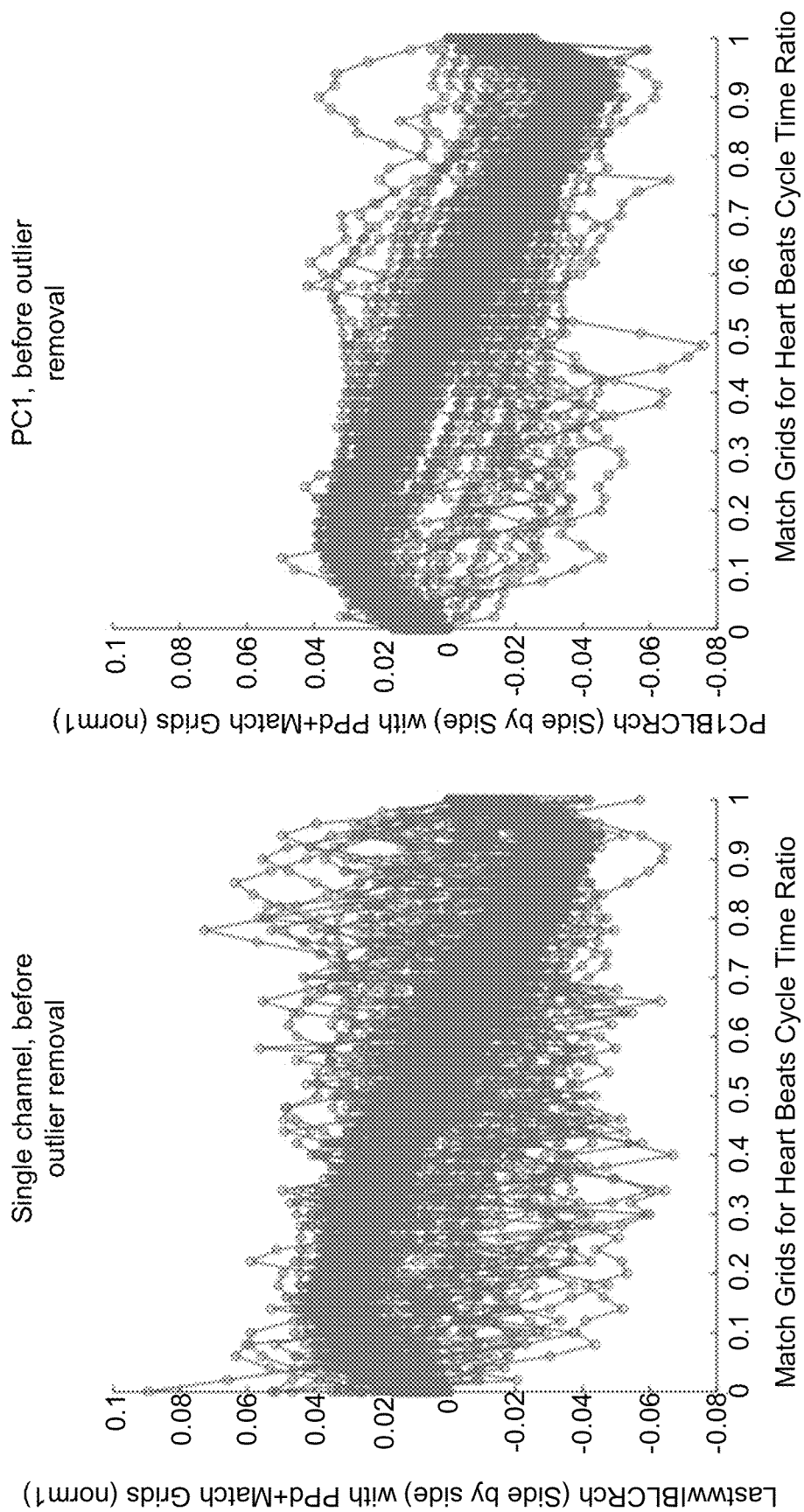
Figure 8D:
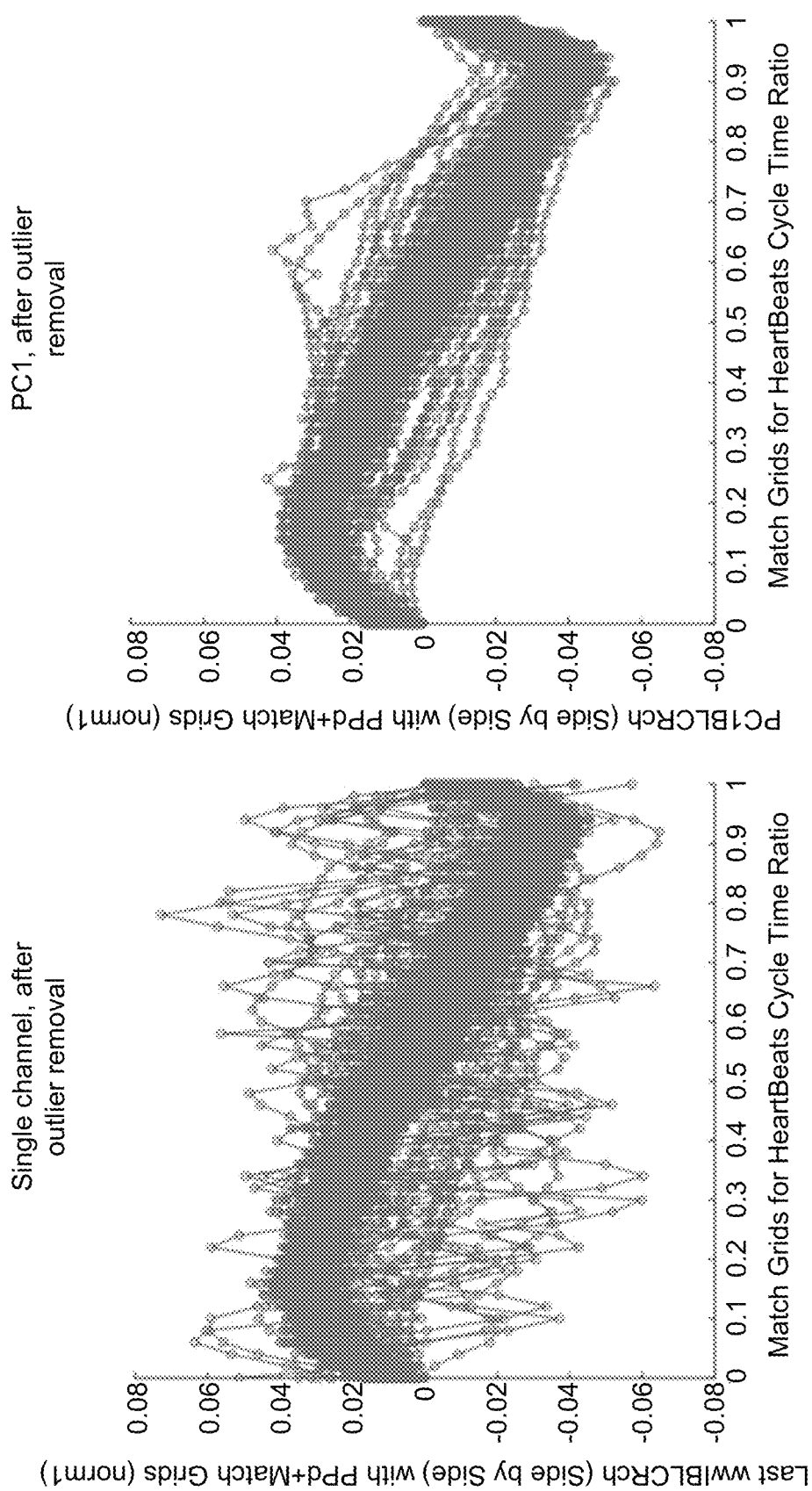

FIGS. 8C and 8D are diagrams illustrating an example of the effect of removing heartbeat cycle outliers for both a single channel scenario and a PC1 scenario. Notably, identification of the individual heartbeat cycles is not necessary for understanding the concept illustrated by FIGS. 8C and 8D; consequently, clear delineation of each heartbeat cycle is not shown. As can be seen based on comparing FIGS. 8C and 8D, PC1 combined with removal of heartbeat cycle outliers in the manner described above provides an improved signal (e.g., as compared to single channel without outlier removal, PC1 without outlier removal, and single channel with outlier removal).

In some implementations, the heartbeat cycle data device may be configured to remove heartbeat cycle outliers in another manner. For example, the heartbeat cycle data device may be configured to remove heartbeat cycle outliers using a chemometric outlier removal method, such as Mahalanobis Distance, Q-residuals, Hotelling's T-Square, Median Absolute Deviation (MAD), a single class support vector machine (SVM), and/or the like.

As indicated above, FIGS. 8A-8D are provided merely as examples. Other examples may differ from what is described with regard to FIGS. 8A-8D.

Figure 9:
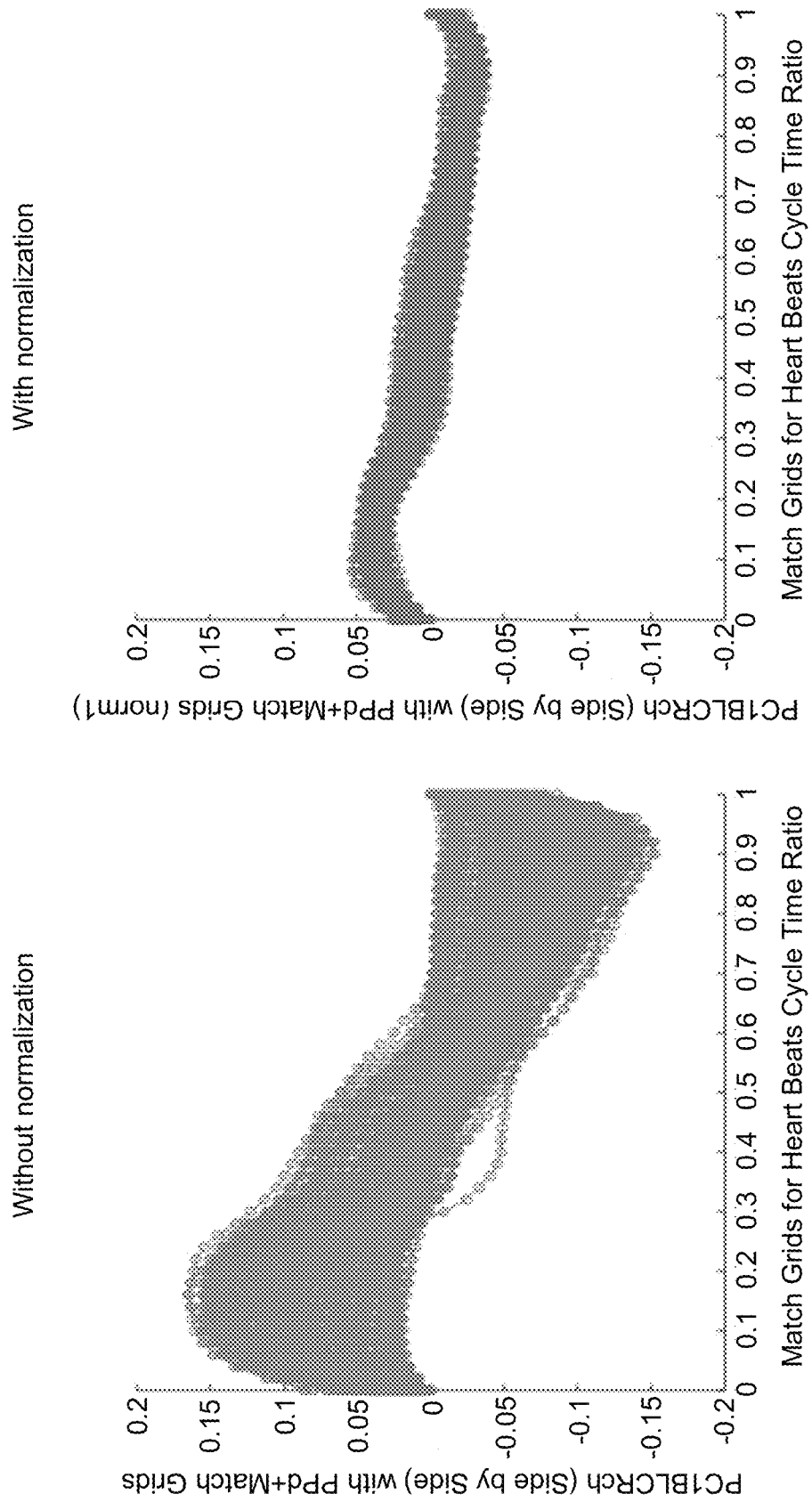
FIG. 9 is a diagram illustrating an example of an effect of applying normalization before generating the baseline corrected heartbeat profile.

In some implementations, the heartbeat cycle data device may be configured to normalize a result of baseline correcting each of the N wavelength channels prior to generating the baseline corrected heartbeat profile using PCA. Normalization in which spectra are divided by areas under their curves to remove an effect of varying photometric responses incurred during sampling. FIG. 9 is a diagram illustrating an example of an effect of applying normalization before generating the baseline corrected heartbeat profile. As can be seen based on comparing the left and right portions of FIG. 9, normalization can be effective in reducing variations occurring during sampling, which results in an improved PC1 result.

As indicated above, FIG. 9 is provided merely as an example. Other examples may differ from what is described with regard to FIG. 9.

Figure 10:
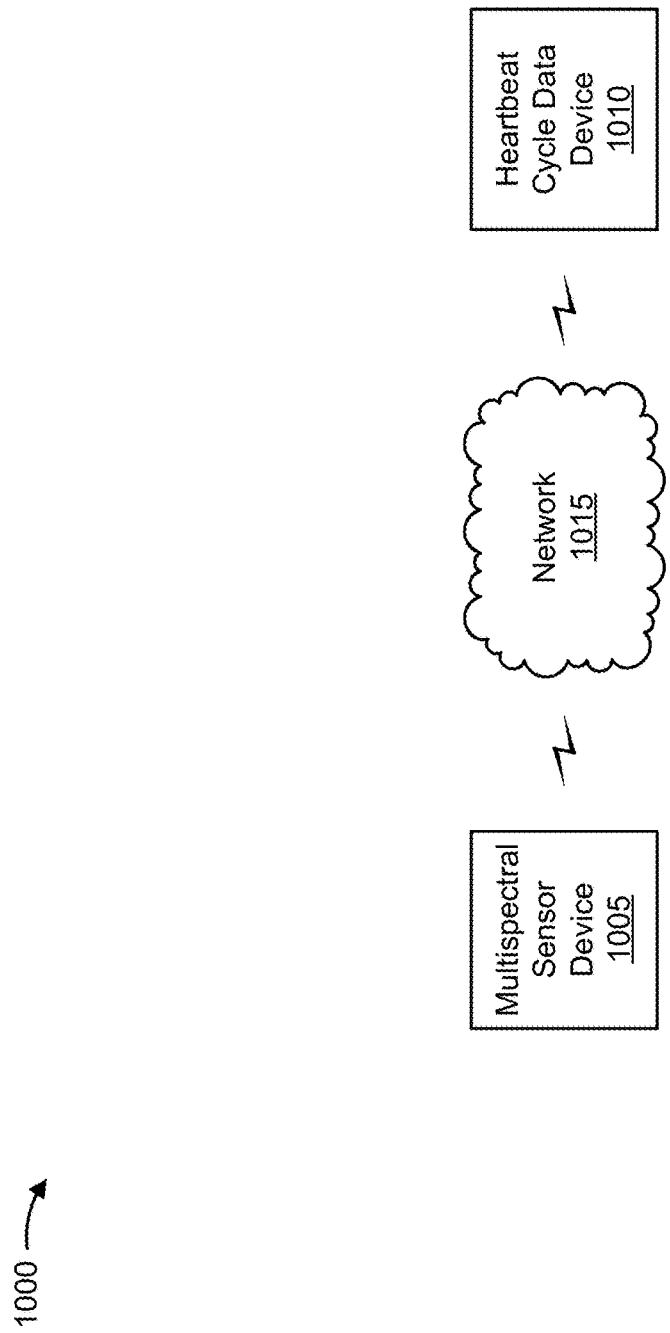
FIG. 10 is a diagram of an example environment in which systems and/or methods described herein may be implemented.

FIG. 10 is a diagram of an example environment 1000 in which systems and/or methods described herein may be implemented. As shown in FIG. 10, environment 1000 may include a multispectral sensor device 1005, a heartbeat cycle data device 1010, and a network 1015. Devices of environment 1000 may interconnect via wired connections, wireless connections, or a combination of wired and wireless connections.

Multispectral sensor device 1005 includes a device capable of measuring, gathering, collecting, or otherwise determining PPG data associated with a plurality of wavelength channels, as described herein. For example, multispectral sensor device 1005 may include a multispectral sensing device capable of determining PPG data (in the form of multivariate time-series data) on each of 64 wavelength channels. In some implementations, multispectral sensor device 1005 may operate in the visible spectrum, the near infrared spectrum, the infrared spectrum, and/or the like. In some implementations, multispectral sensor device 1005 may be a wearable device (e.g., a device worn that can be worn on a wrist, a finger, an arm, a leg, a head, an ear, and/or the like). In some implementations, multispectral sensor device 1005 may be integrated with heartbeat cycle data device 1010 (e.g., such that multispectral sensor device 1005 and heartbeat cycle data device 1010 are on the same chip, in the same package, in the same housing, and/or the like). Alternatively, in some implementations, multispectral sensor device 1005 may be separate from heartbeat cycle data device 1010. In some implementations, multispectral sensor device 1005 may receive information from and/or transmit information to another device in environment 1000, such as heartbeat cycle data device 1010.

Heartbeat cycle data device 1010 includes a device capable of performing one or more operations associated with baseline correcting a heartbeat profile, as described herein. For example, heartbeat cycle data device 1010 may include an application specific integrated circuit (ASIC), an integrated circuit, a server, a group of servers, and/or the like, and/or another type of communication and/or computing device. In some implementations, heartbeat cycle data device 1010 may be integrated with multispectral sensor device 1005 (e.g., such that multispectral sensor device 1005 and heartbeat cycle data device 1010 are on the same chip, in the same package, in the same housing, and/or the like). Alternatively, in some implementations, heartbeat cycle data device 1010 may be separate from multispectral sensor device 1005. In some implementations, heartbeat cycle data device 1010 may receive information from and/or transmit information to another device in environment 1000, such as multispectral sensor device 1005.

Network 1015 includes one or more wired and/or wireless networks. For example, network 1015 may include a wired network (e.g., when multispectral sensor device 1005 and heartbeat cycle data device 1010 are included in same package and/or a same chip). As another example, network 1015 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 10 are provided as an example. In practice, there may be additional devices and/or networks, fewer devices and/or networks, different devices and/or networks, or differently arranged devices and/or networks than those shown in FIG. 10. Furthermore, two or more devices shown in FIG. 10 may be implemented within a single device, or a single device shown in FIG. 10 may be implemented as multiple, distributed devices. Additionally, or alternatively, a set of devices (e.g., one or more devices) of environment 1000 may perform one or more functions described as being performed by another set of devices of environment 1000.

Figure 11:
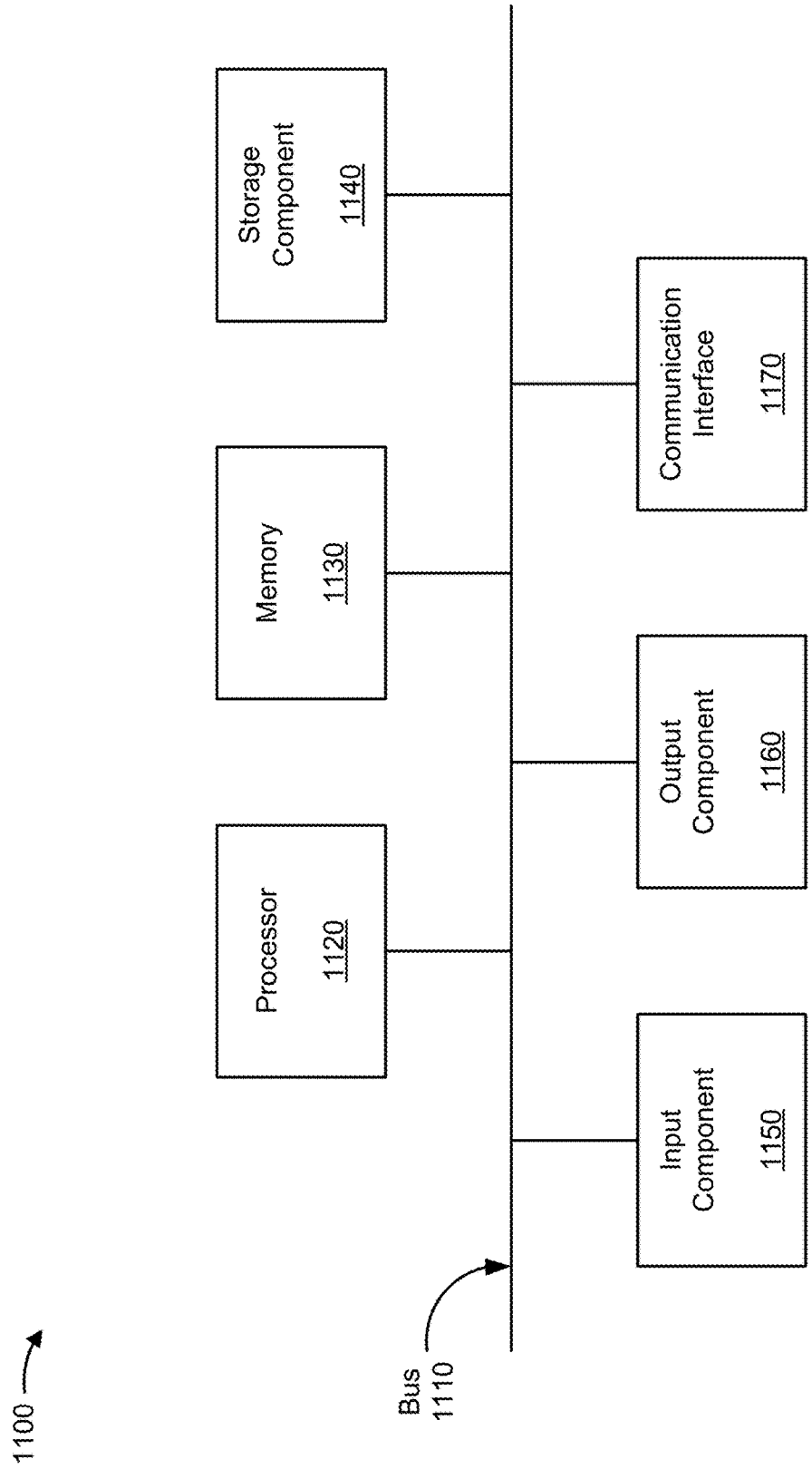
FIG. 11 is a diagram of example components of one or more devices of FIG. 10.

FIG. 11 is a diagram of example components of a device 1100. Device 1100 may correspond to multispectral sensor device 1005 and/or heartbeat cycle data device 1010. In some implementations, multispectral sensor device 1005 and/or heartbeat cycle data device 1010 may include one or more devices 1100 and/or one or more components of device 1100. As shown in FIG. 11, device 1100 may include a bus 1110, a processor 1120, a memory 1130, a storage component 1140, an input component 1150, an output component 1160, and a communication interface 1170.

Bus 1110 includes a component that permits communication among multiple components of device 1100. Processor 1120 is implemented in hardware, firmware, and/or a combination of hardware and software. Processor 1120 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 1120 includes one or more processors capable of being programmed to perform a function. Memory 1130 includes a random access memory (RAM), a read only memory (ROM), and/or another type of dynamic or static storage device (e.g., a flash memory, a magnetic memory, and/or an optical memory) that stores information and/or instructions for use by processor 1120.

Storage component 1140 stores information and/or software related to the operation and use of device 1100. For example, storage component 1140 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 1150 includes a component that permits device 1100 to receive information, such as via user input (e.g., a touch screen display, a keyboard, a keypad, a mouse, a button, a switch, and/or a microphone). Additionally, or alternatively, input component 1150 may include a component for determining location (e.g., a global positioning system (GPS) component) and/or a sensor (e.g., an accelerometer, a gyroscope, an actuator, another type of positional or environmental sensor, and/or the like). Output component 1160 includes a component that provides output information from device 1100 (via, e.g., a display, a speaker, a haptic feedback component, an audio or visual indicator, and/or the like).

Communication interface 1170 includes a transceiver-like component (e.g., a transceiver, a separate receiver, a separate transmitter, and/or the like) that enables device 1100 to communicate with other devices, such as via a wired connection, a wireless connection, or a combination of wired and wireless connections. Communication interface 1170 may permit device 1100 to receive information from another device and/or provide information to another device. For example, communication interface 1170 may include an Ethernet interface, an optical interface, a coaxial interface, an infrared interface, a radio frequency (RF) interface, a universal serial bus (USB) interface, a Wi-Fi interface, a cellular network interface, and/or the like.

Device 1100 may perform one or more processes described herein. Device 1100 may perform these processes based on processor 1120 executing software instructions stored by a non-transitory computer-readable medium, such as memory 1130 and/or storage component 1140. As used herein, the term "computer-readable medium" refers to a non-transitory memory device. A memory device includes memory space within a single physical storage device or memory space spread across multiple physical storage devices.

Software instructions may be read into memory 1130 and/or storage component 1140 from another computer-readable medium or from another device via communication interface 1170. When executed, software instructions stored in memory 1130 and/or storage component 1140 may cause processor 1120 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 11 are provided as an example. In practice, device 1100 may include additional components, fewer components, different components, or differently arranged components than those shown in FIG. 11. Additionally, or alternatively, a set of components (e.g., one or more components) of device 1100 may perform one or more functions described as being performed by another set of components of device 1100.

Figure 12:
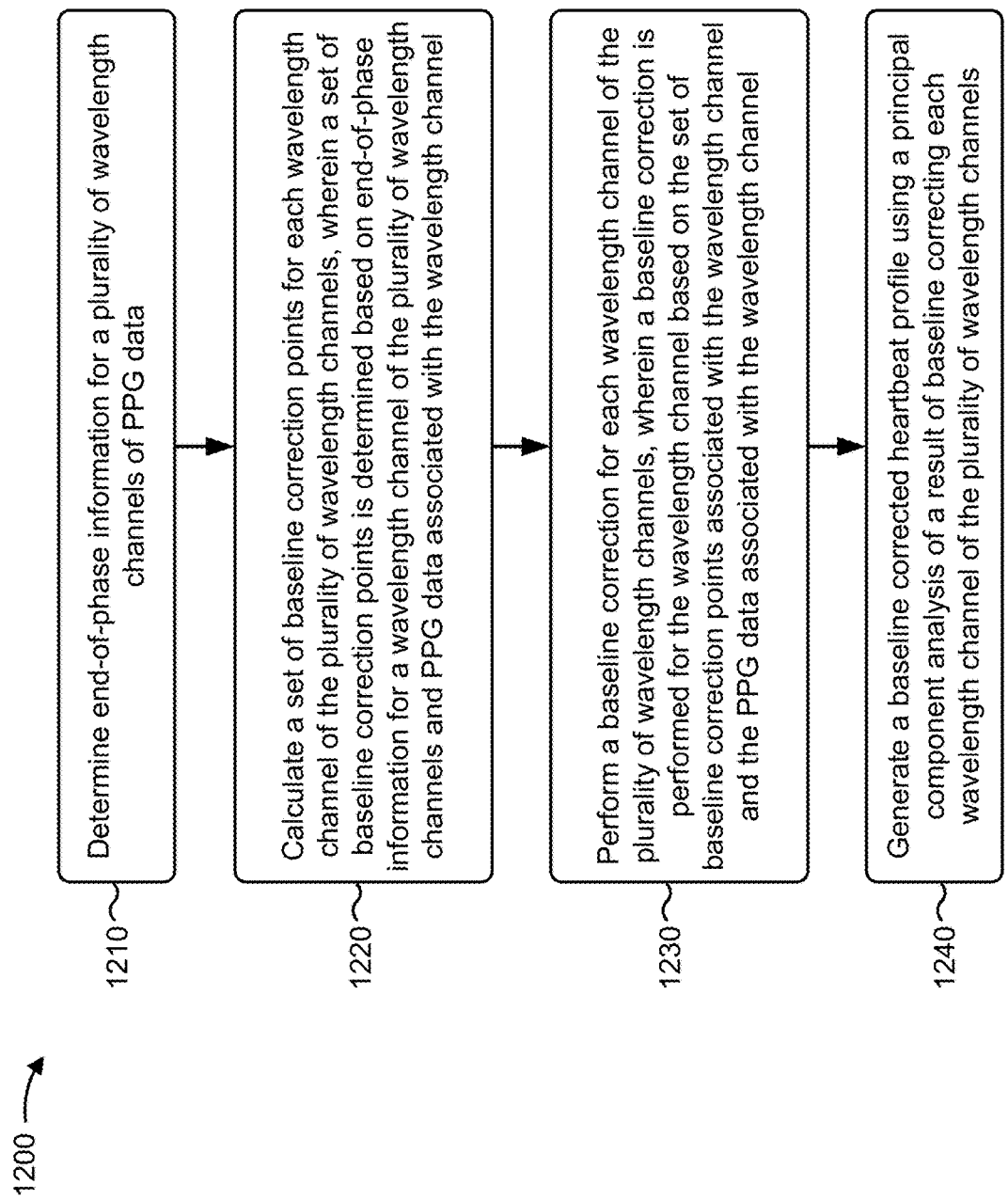
FIG. 12 is a flow chart of an example process for generating a baseline corrected heartbeat profile, as described herein.

FIG. 12 is a flow chart of an example process 1200 for generating a baseline corrected heartbeat profile, as described herein. In some implementations, one or more process blocks of FIG. 12 may be performed by a heartbeat cycle data device (e.g., heartbeat cycle data device 1010). In some implementations, one or more process blocks of FIG. 12 may be performed by another device or a group of devices separate from or including the heartbeat cycle data device, such as a multispectral sensor device (e.g., multispectral sensor device 1005), and/or the like.

As shown in FIG. 12, process 1200 may include determining end-of-phase information for a plurality of wavelength channels of PPG data (block 1210). For example, the heartbeat cycle data device (e.g., using processor 320, memory 330, storage component 340, input component 350, output component 360, communication interface 370 and/or the like) may determine end-of-phase information for a plurality of wavelength channels of PPG data, as described above.

As further shown in FIG. 12, process 1200 may include calculating a set of baseline correction points for each wavelength channel of the plurality of wavelength channels (block 1220). For example, the heartbeat cycle data device (e.g., using processor 320, memory 330, storage component 340, input component 350, output component 360, communication interface 370 and/or the like) may calculate a set of baseline correction points for each wavelength channel of the plurality of wavelength channels, as described above. In some implementations, a set of baseline correction points is calculated based on end-of-phase information for a wavelength channel of the plurality of wavelength channels and PPG data associated with the wavelength channel.

As further shown in FIG. 12, process 1200 may include performing a baseline correction for each wavelength channel of the plurality of wavelength channels (block 1230). For example, the heartbeat cycle data device (e.g., using processor 320, memory 330, storage component 340, input component 350, output component 360, communication interface 370 and/or the like) may perform a baseline correction for each wavelength channel of the plurality of wavelength channels, as described above. In some implementations, a baseline correction is performed for the wavelength channel based on the set of baseline correction points associated with the wavelength channel and the PPG data associated with the wavelength channel.

As further shown in FIG. 12, process 1200 may include generating a baseline corrected heartbeat profile using a principal component analysis of a result of baseline correcting each wavelength channel of the plurality of wavelength channels (block 1240). For example, the heartbeat cycle data device (e.g., using processor 320, memory 330, storage component 340, input component 350, output component 360, communication interface 370 and/or the like) may generate a baseline corrected heartbeat profile using a principal component analysis of a result of baseline correcting each wavelength channel of the plurality of wavelength channels, as described above.

Process 1200 may include additional implementations, such as any single implementation or any combination of implementations described below and/or in connection with one or more other processes described elsewhere herein.

In some implementations, process 1200 includes calculating a set of baseline correction points for the baseline corrected heartbeat profile, and performing, using the set of baseline correction points for the baseline corrected heartbeat profile, a baseline correction for the baseline corrected heartbeat profile.

In some implementations, the end-of-phase information includes end-of-negative-phase information, and the set of baseline correction points for each wavelength channel is a set of trough points for each wavelength channel.

In some implementations, the end-of-phase information includes end-of-positive-phase information, and the set of baseline correction points for each wavelength channel is a set of peak points for each wavelength channel.

In some implementations, the end-of-phase information includes end-of-positive-phase information for the plurality of wavelength channels and end-of-negative-phase information for the plurality of wavelength channels, and the set of baseline correction points for each wavelength channel is a set of centerline points for each wavelength channel. Here, a set of centerline points for a wavelength channel of the plurality of wavelength channels is calculated based on a set of trough points associated with the wavelength channel and a set of peak points associated with the wavelength channel.

In some implementations, a set of centerline points for a wavelength channel of the plurality of wavelength channels is a set of exact crossing points.

In some implementations, the set of centerline points for the wavelength channel is calculated based on removing all negative-to-positive crossings between a peak point, of the set of peak points, and a subsequent trough point of the set of trough points, and removing all but a last negative-to-positive crossing between a trough point, of the set of trough points, and a subsequent peak point of the set of peak points.

In some implementations, process 1200 includes identifying a heartbeat cycle as a heartbeat cycle outlier based on baseline correcting each wavelength channel of the plurality of wavelength channels, and removing the heartbeat cycle outlier prior to generating the baseline corrected heartbeat profile using the principal component analysis.

In some implementations, the heartbeat cycle is identified as a heartbeat cycle outlier based on determining that a period of the heartbeat cycle differs from a popular heartbeat cycle period by an amount that satisfies a threshold.

In some implementations, process 1200 includes normalizing the result of baseline correcting each wavelength channel of the plurality of wavelength channels prior to generating the baseline corrected heartbeat profile using the principal component analysis.

Although FIG. 12 shows example blocks of process 1200, in some implementations, process 1200 may include additional blocks, fewer blocks, different blocks, or differently arranged blocks than those depicted in FIG. 12. Additionally, or alternatively, two or more of the blocks of process 1200 may be performed in parallel.

Some implementations described herein provide a device (e.g., heartbeat cycle data device 1010, multispectral sensor device 1005, and/or the like) capable of generating a baseline corrected heartbeat profile. As described above, the baseline corrected heartbeat profile is a heartbeat profile for which sloping baselines and/or baseline shifts have been at least partially corrected (e.g., so as to reduce or eliminate an impact of the sloping baselines and/or baseline shifts on the heartbeat profile). In some implementations, the baseline corrected heartbeat profile can be used in association with performing a biometric monitoring action, such as vital sign monitoring (e.g., instantaneous heart rate determination, blood pressure determination, and/or the like), or another type of biometric determination and/or monitoring (e.g., blood oxygenation determination, augmentation index determination, hydration determination, and/or the like) with improved accuracy and/or reliability, as described above.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method comprising:
 receiving, by a device, photoplethysmography data for a plurality of wavelength channels; and
 providing, by the device, one or more of:
  a baseline corrected heartbeat profile that is based on a baseline correction performed for a wavelength channel, of the plurality of wavelength channels, using a set of baseline correction points associated with the wavelength channel, or
  information associated with the baseline corrected heartbeat profile.

2. The method of claim 1, wherein the photoplethysmography data includes photometric response data.

3. The method of claim 2, wherein the photometric response data indicates a blood volume beneath a skin surface at a location of a multispectral sensor device at a time point.

4. The method of claim 1, wherein the plurality of wavelength channels comprises 64 channels.

5. The method of claim 1, wherein receiving the photoplethysmography data comprises:
 receiving the photoplethysmography data from a multispectral sensor device that is configured to be worn on a wrist.

6. The method of claim 5, wherein the multispectral sensor device and the device are integrated within a same package or a same housing.

7. The method of claim 1, further comprising:
 determining end-of-phase information for the plurality of wavelength channels;
 calculating the set of baseline correction points for the wavelength channel;
 performing the baseline correction for the wavelength channel based on the set of baseline correction points and at least a portion of the photoplethysmography data associated with the wavelength channel; and
 generating the baseline corrected heartbeat profile by performing a principal component analysis (PCA) on results of baseline correcting the plurality of wavelength channels,
  wherein the results include a result of performing the baseline correction for the wavelength channel.

8. The method of claim 7, wherein the end-of-phase information includes, for the wavelength channel, one or more of:
 information that identifies end points of positive phases in the photoplethysmography data, or
 information that identifies end points of negative phases in the photoplethysmography data; and
 wherein the set of baseline correction points includes a set of points that define a baseline of the photoplethysmography data for the wavelength channel.

9. The method of claim 1, wherein providing one or more of the baseline corrected heartbeat profile or the information associated with the baseline corrected heartbeat profile comprises:
 providing, to a device configured to perform vital sign monitoring, the information associated with the baseline corrected heartbeat profile,
  wherein the information associated with the baseline corrected heartbeat profile comprises an instantaneous heart rate that is based on the baseline corrected heartbeat profile.

10. The method of claim 1, wherein providing one or more of the baseline corrected heartbeat profile or the information associated with the baseline corrected heartbeat profile comprises:
 providing, to a device configured to perform biometric monitoring, the baseline corrected heartbeat profile,
  wherein the biometric monitoring comprises one or more of blood oxygen saturation determination or hydration determination.

11. A device, comprising:
 one or more memories; and
 one or more processors, coupled to the one or more memories, configured to:
  receive photoplethysmography data for one or more wavelength channels; and
  provide one or more of:
   a baseline corrected heartbeat profile that is based on a baseline correction for a wavelength channel of the one or more wavelength channels, or
   information associated with the baseline corrected heartbeat profile.

12. The device of claim 11, wherein the photoplethysmography data includes photometric response data.

13. The device of claim 12, wherein the photometric response data indicates a blood volume beneath a skin surface at a location of a multispectral sensor device at a time point.

14. The device of claim 11, wherein the one or more wavelength channels comprises 64 channels.

15. The device of claim 11, wherein the one or more processors, to receive the photoplethysmography data, are configured to:
 receive the photoplethysmography data from a multispectral sensor device that is configured to be worn on a wrist.

16. The device of claim 11, wherein the one or more processors are further configured to:
 determine end-of-phase information for the one or more wavelength channels;
 calculate a set of baseline correction points for the wavelength channel;
 perform the baseline correction for the wavelength channel based on the set of baseline correction points and at least a portion of the photoplethysmography data associated with the wavelength channel; and
 generate the baseline corrected heartbeat profile by performing a principal component analysis (PCA) on results of baseline correcting the one or more wavelength channels,
  wherein the results include a result of performing the baseline correction for the wavelength channel.

17. The device of claim 16, wherein the end-of-phase information includes, for the wavelength channel, one or more of:
 information that identifies end points of positive phases in the photoplethysmography data, or
 information that identifies end points of negative phases in the photoplethysmography data; and
 wherein the set of baseline correction points includes a set of points that define a baseline of the photoplethysmography data for the wavelength channel.

18. The device of claim 11, wherein the one or more processors, to provide one or more of the baseline corrected heartbeat profile or the information associated with the baseline corrected heartbeat profile, are configured to:
provide, to a device configured to perform vital sign monitoring, the information associated with the baseline corrected heartbeat profile,
wherein the information associated with the baseline corrected heartbeat profile comprises an instantaneous heart rate that is based on the baseline corrected heartbeat profile.

19. The device of claim 11, wherein the one or more processors, to provide one or more of the baseline corrected heartbeat profile or the information associated with the baseline corrected heartbeat profile, are configured to:
provide, to a device configured to perform biometric monitoring, the baseline corrected heartbeat profile,
wherein the biometric monitoring comprises one or more of blood oxygen saturation determination or hydration determination.

20. A non-transitory computer-readable medium storing a set of instructions, the set of instructions comprising:
one or more instructions that, when executed by one or more processors of a device, cause the device to:
receive photoplethysmography data for a plurality of wavelength channels; and
provide one or more of:
a baseline corrected heartbeat profile that is based on a baseline correction for a wavelength channel of the plurality of wavelength channels, or
information associated with the baseline corrected heartbeat profile.

* * * * *